United States Patent
Jung et al.

(10) Patent No.: US 10,253,082 B2
(45) Date of Patent: Apr. 9, 2019

(54) LONG-ACTING INSULIN AND USE THEREOF

(71) Applicant: HANMI PHARM. CO., LTD., Gyeonggi-do (KR)

(72) Inventors: Sung Youb Jung, Gyeonggi-do (KR); Sang Youn Hwang, Gyeonggi-do (KR); Euh Lim Oh, Gyeonggi-do (KR); Sung Hee Park, Gyeonggi-do (KR); Hyun Uk Kim, Busan (KR); Chang Ki Lim, Gyeonggi-do (KR); Se Chang Kwon, Seoul (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.

(21) Appl. No.: 15/113,027

(22) PCT Filed: Jan. 20, 2015

(86) PCT No.: PCT/KR2015/000576
§ 371 (c)(1),
(2) Date: Jul. 20, 2016

(87) PCT Pub. No.: WO2015/108398
PCT Pub. Date: Jul. 23, 2015

(65) Prior Publication Data
US 2017/0101455 A1 Apr. 13, 2017

(30) Foreign Application Priority Data
Jan. 20, 2014 (KR) .................. 10-2014-0006938

(51) Int. Cl.
*A61K 38/28* (2006.01)
*C07K 14/62* (2006.01)
*A61K 38/00* (2006.01)

(52) U.S. Cl.
CPC .............. *C07K 14/62* (2013.01); *A61K 38/00* (2013.01); *C07K 2319/30* (2013.01)

(58) Field of Classification Search
CPC .................................. A61K 38/28; C07K 14/62
See application file for complete search history.

(56) References Cited

U.S. PATENT DOCUMENTS

| | | | |
|---|---|---|---|
| 5,175,145 A | 12/1992 | Cooper | |
| 5,422,339 A * | 6/1995 | Eisenbarth | ............. C07K 14/62 514/6.1 |
| 5,424,286 A | 6/1995 | Eng | |
| 6,403,764 B1 | 6/2002 | Dubaquie et al. | |
| 7,736,653 B2 | 6/2010 | Kim et al. | |
| 7,790,677 B2 | 9/2010 | Zimmerman et al. | |
| 8,476,230 B2 | 6/2013 | Song et al. | |
| 9,165,768 B2 | 10/2015 | Kang | |
| 9,341,445 B2 | 5/2016 | de Haas et al. | |
| 9,422,349 B2 | 8/2016 | Jung et al. | |
| 9,526,764 B2 | 12/2016 | Werner et al. | |
| 9,528,180 B2 | 12/2016 | Becker et al. | |
| 9,669,073 B2 | 6/2017 | Kim et al. | |
| 2005/0288248 A1 | 12/2005 | Pan et al. | |
| 2006/0241019 A1 | 10/2006 | Bridon et al. | |
| 2010/0105877 A1 | 4/2010 | Song et al. | |
| 2010/0216692 A1 | 8/2010 | Brunner-Schwarz et al. | |
| 2011/0077197 A1 | 3/2011 | Habermann et al. | |
| 2011/0152185 A1 | 6/2011 | Plum et al. | |
| 2011/0257091 A1 | 10/2011 | DiMarchi et al. | |
| 2012/0021978 A1 | 1/2012 | Werner et al. | |
| 2012/0071402 A1 | 3/2012 | Madsen et al. | |
| 2012/0100141 A1 | 4/2012 | Herring et al. | |
| 2012/0184488 A1 | 7/2012 | Weiss | |
| 2013/0028918 A1* | 1/2013 | Song ..................... A61K 38/28 424/179.1 |
| 2013/0122023 A1 | 5/2013 | Woo et al. | |
| 2014/0120120 A1 | 5/2014 | Woo et al. | |
| 2014/0212440 A1 | 7/2014 | Jung et al. | |
| 2015/0190528 A1 | 7/2015 | Lim et al. | |
| 2016/0008483 A1 | 1/2016 | Hwang et al. | |
| 2017/0143802 A1 | 5/2017 | Kim et al. | |

FOREIGN PATENT DOCUMENTS

| | | |
|---|---|---|
| CL | 1235-2003 | 4/2004 |
| CL | 00018-2009 | 6/2009 |
| CL | 201603075 | 11/2016 |
| DE | 102 27 232 A1 | 1/2004 |
| DE | 10 2008 003 568 A1 | 7/2009 |
| DE | 10 2008 025 008 A1 | 11/2009 |
| EP | 2017288 A1 | 1/2009 |
| EP | 2700654 A1 | 2/2014 |
| EP | 2963056 A1 | 1/2016 |
| JP | 2009-504169 | 2/2009 |

(Continued)

OTHER PUBLICATIONS

Intellectual Property Office of Singapore, Communication dated Oct. 3, 2017 in related counterpart application No. 11201609564T.
European Patent Office, Communication dated Nov. 10, 2017 in related counterpart application No. 15799334.6.
Chilean Patent Office, Communication dated Jul. 13, 2017 by the Chilean Patent Office in counterpart Chilean Patent Application No. 201601844.
Chu et al., "The A14 Position of Insulin Tolerates Considerable Structural Alterations with Modest Effects on the Biological Behavior of the Hormone", Journal of Protein Chemistry, vol. 11, No. 5, 1992, pp. 571-577.
European Patent Office, Communication dated Sep. 20, 2017 by the European Patent Office in counterpart European Patent Application No. EP 15 73 7856.
Authier, F. et al. (1998). "Uptake and Metabolic Fate of [His$^{48}$, His$^{B4}$, Glu$B10$, His$^{B27}$] Insulin in Rat Liver In Vivo," *Biochem J.* 332:421-30.

(Continued)

*Primary Examiner* — Gyan Chandra
(74) *Attorney, Agent, or Firm* — Sughrue Mion, PLLC

(57) ABSTRACT

The present invention relates to an insulin analog that has reduced insulin receptor binding affinity for the purpose of increasing the blood half-life of insulin, and long-acting insulin, a conjugate, and a method of preparing long-acting insulin using the same.

18 Claims, 6 Drawing Sheets

Specification includes a Sequence Listing.

(56) References Cited

FOREIGN PATENT DOCUMENTS

| | | |
|---|---|---|
| JP | 2011-515358 | 5/2011 |
| JP | 2012-062311 A | 3/2012 |
| JP | 2012-229214 A | 11/2012 |
| KR | 10-2011-0137819 A | 1/2001 |
| KR | 10-2005-0121748 A | 12/2005 |
| KR | 10-0725315 B1 | 6/2007 |
| KR | 10-2010-0111683 A | 10/2010 |
| KR | 10-2011-0084956 A | 7/2011 |
| KR | 10-2011-0092253 A | 8/2011 |
| KR | 10-1058209 B1 | 8/2011 |
| KR | 10-1058290 B1 | 8/2011 |
| KR | 10-2011-0111267 A | 10/2011 |
| KR | 10-2011-0134209 A | 12/2011 |
| KR | 10-2011-0134210 A | 12/2011 |
| KR | 10-2012-0135123 A | 12/2012 |
| KR | 10-2012-0137271 A | 12/2012 |
| KR | 10-2012-0139579 A | 12/2012 |
| KR | 10-1231431 B1 | 2/2013 |
| KR | 10-1324828 B1 | 11/2013 |
| KR | 10-1330868 B1 | 11/2013 |
| KR | 10-2014-0006938 A | 1/2014 |
| KR | 10-2014-0022909 A | 2/2014 |
| KR | 10-2014-0106452 A | 9/2014 |
| TW | 201204382 A1 | 2/2012 |
| WO | WO-1996/32478 A1 | 10/1996 |
| WO | WO-1997/34631 A1 | 9/1997 |
| WO | 2009/129250 | 10/2000 |
| WO | 2009/022005 | 2/2009 |
| WO | 2010/080606 A1 | 7/2010 |
| WO | 2010/080609 | 7/2010 |
| WO | 2011/028813 A2 | 3/2011 |
| WO | 2011/122921 A2 | 10/2011 |
| WO | 2012/015692 A2 | 2/2012 |
| WO | 2012/098462 A1 | 7/2012 |
| WO | 2012/165915 A2 | 12/2012 |
| WO | 2012/167251 A1 | 12/2012 |
| WO | 2012/169798 A2 | 12/2012 |
| WO | 2012/173422 A1 | 12/2012 |
| WO | 2013/110069 A1 | 7/2013 |
| WO | 2013/133667 A1 | 9/2013 |
| WO | 2014/017843 A1 | 1/2014 |
| WO | 2014/017845 A2 | 1/2014 |
| WO | 2014/017847 A1 | 1/2014 |
| WO | 2014/017849 A1 | 1/2014 |
| WO | 2014/049610 A2 | 4/2014 |
| WO | 2014/073842 A1 | 5/2014 |
| WO | 2014/133324 A1 | 9/2014 |
| WO | 2015/183038 A1 | 12/2015 |

OTHER PUBLICATIONS

Brange, J. et al. (Sep. 1990). "Monomeric Insulins and Their Experimental and Clinical Implications," *Diabetes Care* 13(9):923-54, Abstract Only.

Duckworth, W.C. et al. (Oct. 1998). "Insulin Degradation: Progress and Potential," *Endocr Rev.* 19(5):608-24.

Lin, S. et al. (Aug. 1998). "Comparative Pharmacokinetic and Pharmacodynamic Studies of Human Insulin and Analogues in Chronic Diabetic Yucatan Minipigs," *J Pharmacol Exp Ther* 286(2):959-66.

Ribel, U. et al. (Sep. 1990). "Equivalent in Vivo Biological Activity of Insulin Analogues and Human Insulin Despite Different in Vitro Potencies," *Diabetes* 39:1033-9.

Uhlman, E. et al. (Jun. 1990). "Antisense Oligonucleotides: A New Therapeutic Principle," *Chemical Reviews* 90(4):544-584.

Valera, M. M. et al. (Dec. 2003). "Insulin Clearance in Obesity," *J Am Coll Nutr*. 22(6):487-93, Abstract Only.

Jørgensen, A. et al (Apr. 1996). "Solution Structure of the Superactive Monomeric Des-[Phe(B25)] Human Insulin Mutant: Elucidation of the Structural Basis for the Monomerization of Des-[Phe(B25)] Insulin and the Dimerization of Native Insulin," 257(3):684-699.

Keller, D. et al. (2001). "Flexibility and Bioactivity of Insulin: an NMR Investigation of the Solution Structure and Folding of an Unusually Flexible Human Insulin Mutant with Increased Biological Activity," Biochemistry 40(35):10732-10740.

NCBI, Genbank AAA72172.1, (Apr. 27, 1993)/ "Synthetic Preproinsulin [synthetic construct] NCBI," located at https://www.ncbi.nlm.nih.gov/protein/AAA72172.1?report=gpwithparts&log$=seqview, last visited on Jun. 20, 2017.

NCBI, Genbank AKI70564.1 (Jun. 1, 2015). "INS, Partial [synthetic construct]" located at <https://www.ncbi.nlm.nih.gov/protein/AKI70564.1?report=gpwithparts&log$=seqview> last visited on Jun. 20, 2017.

NCBI, Genbank NM_001291897.1, (May 13, 2015). "*Homo sapiens* Insulin (INS), Transcript Variant 4, mRNA," located at < https://www.ncbi.nlm.nih.gov/nuccore/NM-001291897.1?report=gpwithparts&log$=seqview&sat=4&satkey=139944924>, last visited on Jun. 20, 2017, 4 pages.

United States Patent and Trademark Office Communication dated Sep. 8, 2017 in counterpart U.S. Appl. No. 15/313,501.

European Patent Office; Communication dated May 10, 2017, in counterpart European application No. 14757629.2.

United States Patent and Trademark Office communication dated Jan. 17, 2017 in counterpart U.S. Appl. No. 14/769,495.

United States Patent and Trademark Office communication dated Jul. 19, 2017 in counterpart U.S. Appl. No. 14/769,495.

Chen et al., "Four New Monomeric Insulins Obtained by Alanine Scanning the Dimer-Forming Surface of the Insulin Molecule," Protein Eng'g 13:779-782 (2000).

Nakagawa et al., "Chiral Mutagenesis of Insulin, Contribution of the B20-B23 β-turn to Activity and Stability," J. Biol. Chem. 281:22386-22396, (2006).

United States Patent and Trademark Office communication dated Sep. 14, 2017 in counterpart U.S. Appl. No. 15/250,459.

UniProtKB A6XGL2, pp. 1-5. Integrateded in UniProtKB/TrEMBL Aug. 21, 2007.

Yampolsky et al., "The Exchangeability of Amino Acids in Proteins," Genetics, 170: 1459-1472, 2005.

Rudinger J., "Characteristics of the Amino Acids as Components of a Peptide Hormone Sequence," Peptide Hormones, J.A. Parsons Edition, University Park Press, Jun. 1976, pp. 1-7. (8 pages total).

"Designing Custom Peptides," from SIGMA Genosys, pp. 1-2. Accessed Dec. 16, 2004.

Schinzel R., Drueckes P., "The Phosphate Recognition Site of *Escherichia coli* Maltodextrin Phosphorylase," FEBS, Jul. 1991. 286(1,2): 125-128.

Berendsen HJC, "A Glimpse of the Holy Grail?" Science, 1998, 282: 642-643.

Voet D, Voet JG, Biochemistry, Second Edition, John Wiley & Sons, Inc., 1995, pp. 235-241. (9 pages).

Ngo J.T., Marks J, Karplus M., "Computational Complexity, Protein Structure Prediction, and the Levinthal Paradox," The Protein Folding Problem and Teritary Structure Prediction, K. Merc Jr. and S. Le Grand Edition, 1994, pp. 491-495.

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.

Betts et al., "Amino Acid Properties and Consequences of Substitutions," Bioinformatics for Geneticists, Chapter 14, John Wiley & Sons, LTd., 2003, pp. 289-316.

Mohan. "Which Insulin to Use? Human or Animal?," Curr. Sci, 83:1544-1547 (2002).

European Patent Office; Communication dated Nov. 30, 2016, in counterpart European Application No. 14757629.2.

Colombian Patent Office; Communication dated Nov. 8, 2016, in counterpart Colombian application No. 15227010.

Kristensen et al., "Alanine Scanning Mutagenesis of Insulin," The Journal of Biological Chemistry, vol. 272, No. 20, 1997, pp. 12978-12983. (7 pages total).

Chile Patent Office; Communication dated Aug. 22, 2016, issued in corresponding Application No. 2015-002330.

Saudi Arabian Patent Office; Communication dated Apr. 30, 2016, issued in corresponding Application No. 515360933.

(56) References Cited

OTHER PUBLICATIONS

R. Vigneri, et al., "Insulin and its analogs: actions via insulin and IGF receptors", Acta Diabetol, 2010, pp. 271-278, vol. 47, No. 4.
NCBI, "insulin preproprotein [*Homo sapiens*]", NCBI Reference Sequence: NP_000198.1, Feb. 17, 2013, [online]<http://www.ncbi.nlm.nih.gov/protein/4557671?sat=17&satkey=22757282> retrieved on Mar. 31, 2014.
International Searching Authority, International Search Report for PCT/KR2014/001593 dated May 22, 2014.
International Searching Authority, Written Opinion of the International Search Authority for PCT/KR2014/001593 dated May 22, 2014.
Martin Lorenz et al., "Recent progress and future options in the development of GLP-1 receptor agonists for the treatment of diabesity", Bioorganic & Medicinal Chemistry Letters, 2013, pp. 4011-4018, vol. 23, No. 14.
International Searching Authority, International Search Report of PCT/KR2015/005455 dated Aug. 24, 2015 [PCT/ISA/210].
International Searching Authority, Written Opinion of PCT/KR2015/005455 dated Aug. 24, 2015 [PCT/ISA/237].
Colombian Patent Office; Communication dated Aug. 24, 2017, in counterpart Colombian application No. 15227010.
Taiwanese Intellectual Property Office; Communication dated Sep. 11, 2017 in counterpart application No. 103106674.
Fosgerau et al., "Combination of Long-Acting Insulin with the Dual GluGLP-1 Agonist ZP2929 Causes Improved Glycemic Control without Body Weight Gain in db/db Mice", 1527-P, Diabetes (Suppl 1), vol. 60, 2011, p. A418, XP-002775063.

European Patent Office; Communication dated Nov. 17, 2017 in counterpart application No. 15799077.1.
Japanese Patent Office; Communication dated Jan. 16, 2018 in counterpart Japanese application No. 2015-559199.
United States Patent and Trademark Office; Notice of Allowance dated Feb. 26, 2018 in U.S. Appl. No. 15/250,459.
United States Patent and Trademark Office; Final Rejection dated Mar. 8, 2018 in U.S. Appl. No. 15/313,501.
United States Patent and Trademark Office; Non-Final Rejection dated Apr. 5, 2018 in U.S. Appl. No. 14/769,495.
Colombian Patent and Trademark Office; communication dated Feb. 16, 2018, in Colombian application No. NC2016/0004794.
Chinese Patent and Trademark Office; communication dated Mar. 1, 2018, in Chinese Patent Application No. 201480006998.4.
Intellectual Property Office of Singapore; Communication dated Jan. 26, 2018 in counterpart Singaporean application No. 11201609872Y.
United States Patent and Trademark Office; Non-Final Rejection dated Apr. 17, 2018 in co-pending U.S. Appl. No. 15/315,020.
Chilean Patent Office; Communication dated May 24, 2018 issued in counterpart Chilean Application No. 201603069.
Japanese Patent Office; Communication dated Sep. 11, 2018 in application No. 2015-559199.
Japanese Patent Office, Communication dated Nov. 13, 2018 by the Japanese Patent Office in copending Application No. 2016-564933.
Glendorf et al., "Engineering of Insulin Receptor Isoform-Selective Insulin Analogues", PloS One vol. 6, Issue 5, May 2011, e20288.
Chilean Patent Office, communication dated Nov. 14, 2018 by the Chilean Patent Office in copending Application No. 201603069.

* cited by examiner

[FIG. 1]
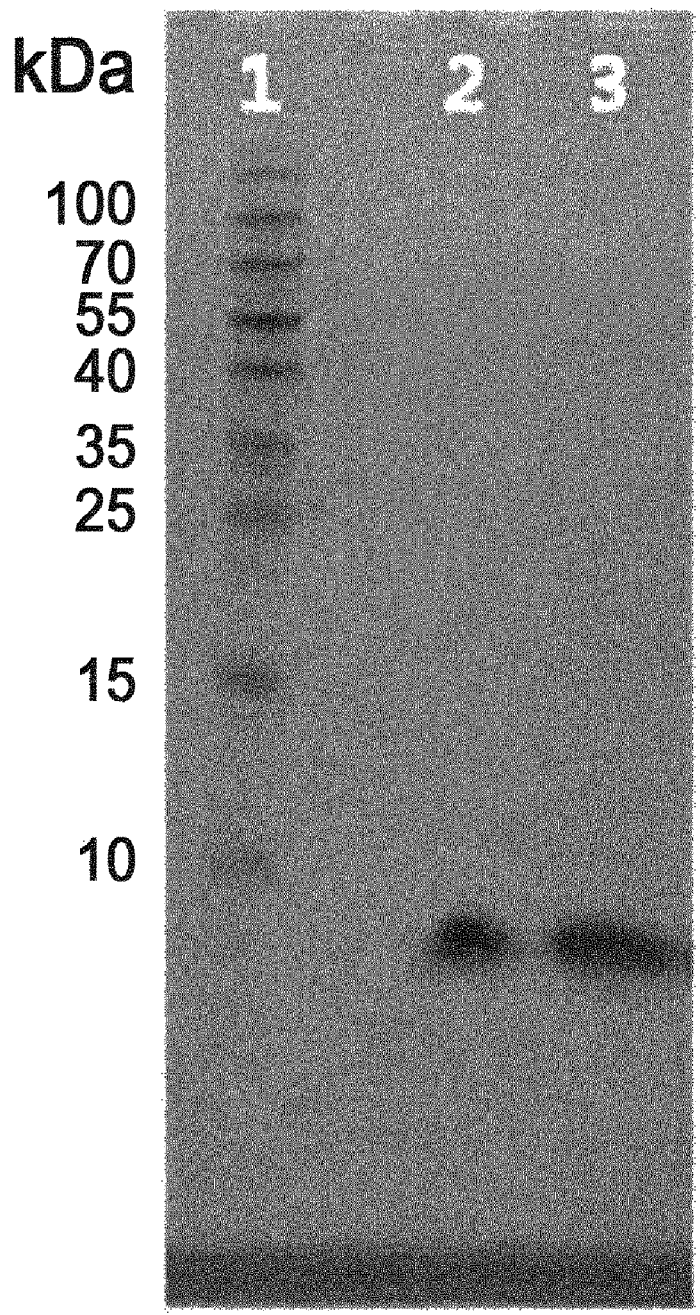

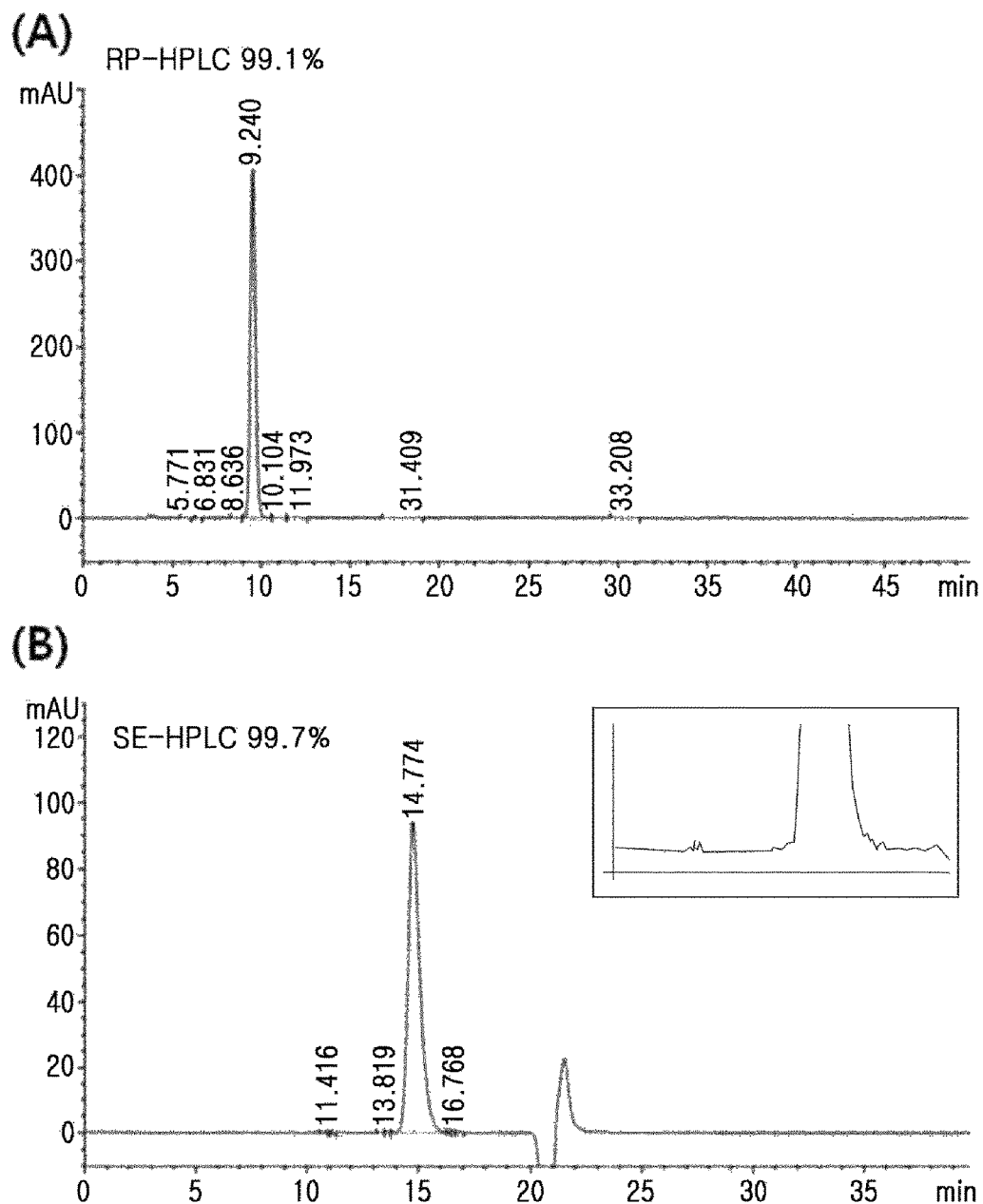

[FIG. 3]
(A) Glu-C cleavage fragment of native insulin sequence
```
              A1        A2         A3
A chain: GIVE QCCTSICSLYQLE NYCN
B chain: FVNQHLCGSHLVE ALYLVCGE RGFFYTPKT
              B1          B2        B3
```
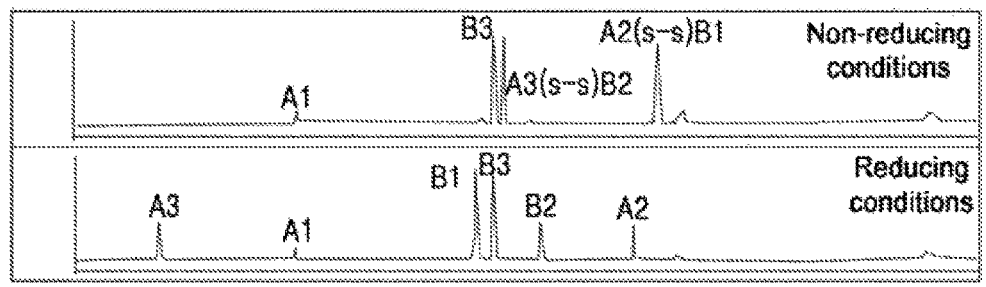
(B) Glu-C cleavage fragment of insulin analog (No. 7) sequence
```
              A1        A2         A3
A chain: GIVE QCCTSICSLYQLE NYCN
B chain: FVNQHLCGSHLVE ALYLVCGE RGFAYTPKT
              B1          B2        B3
```
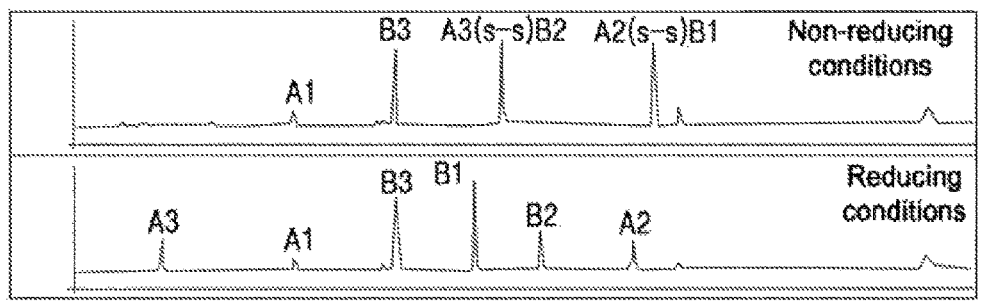

[FIG. 4]
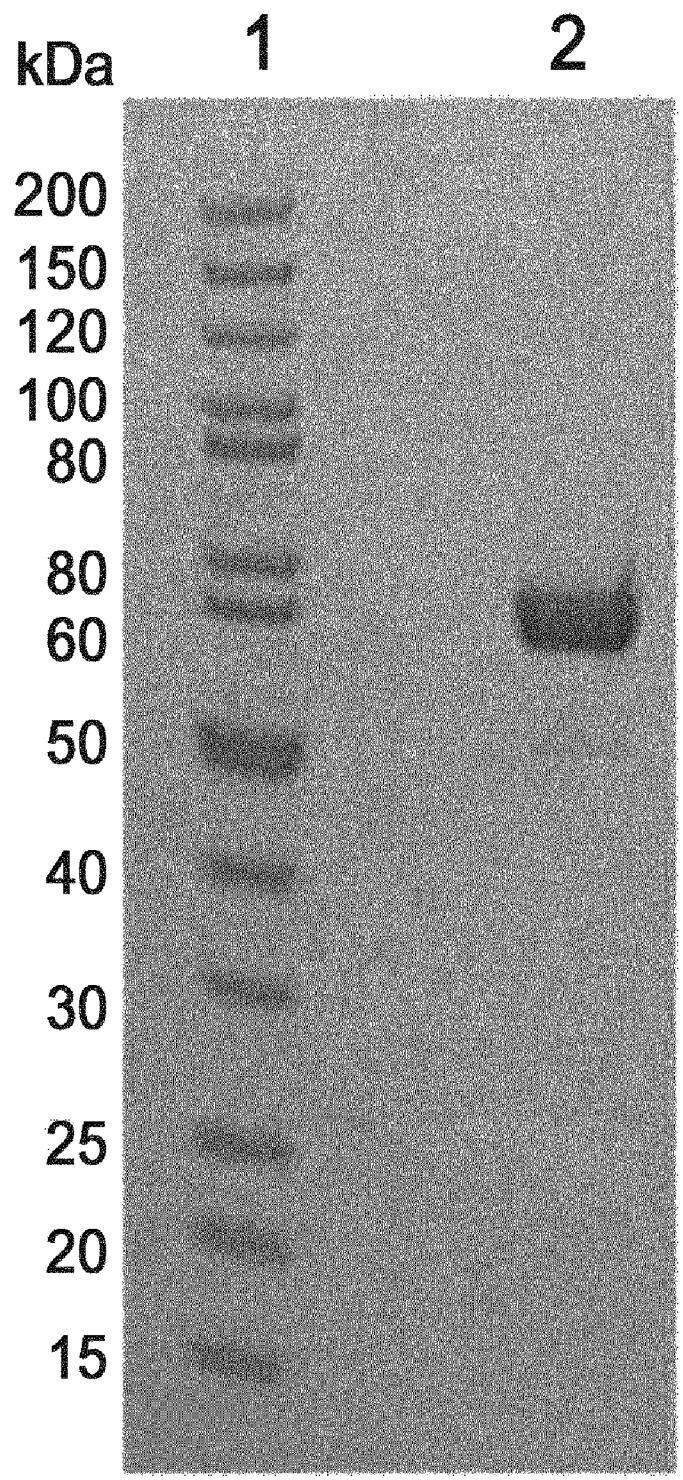

[FIG. 5]
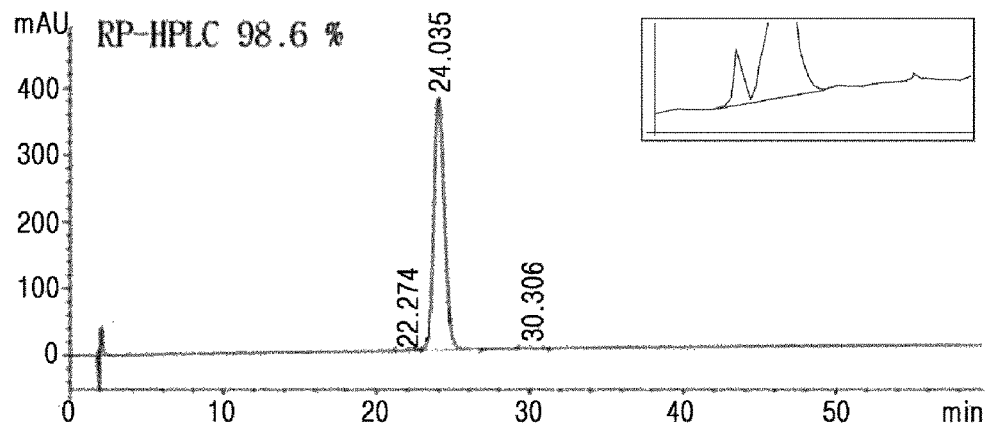
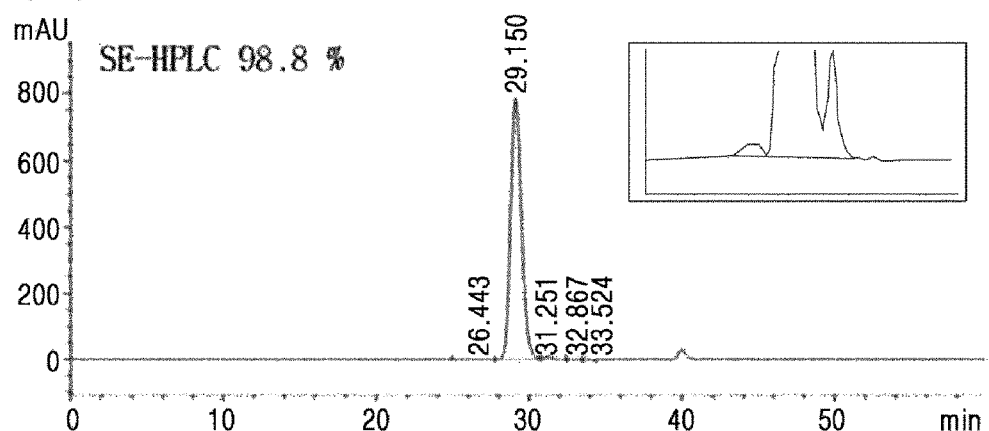
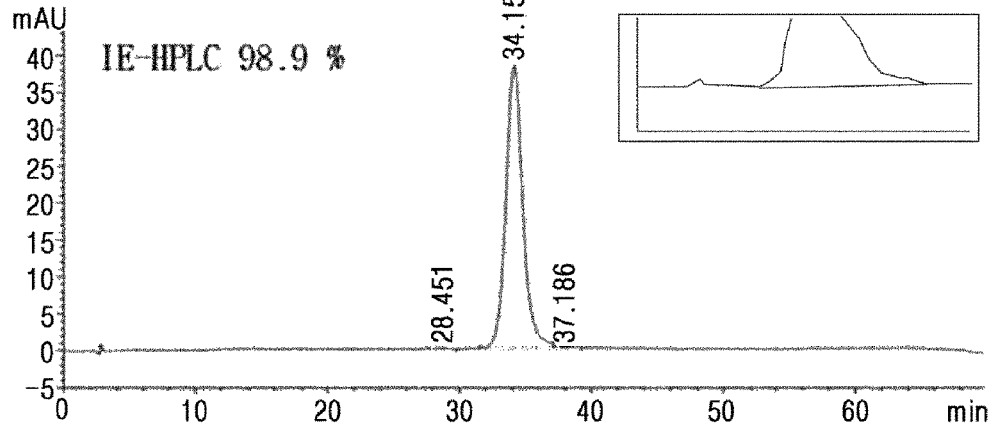

[FIG. 6]
(A)
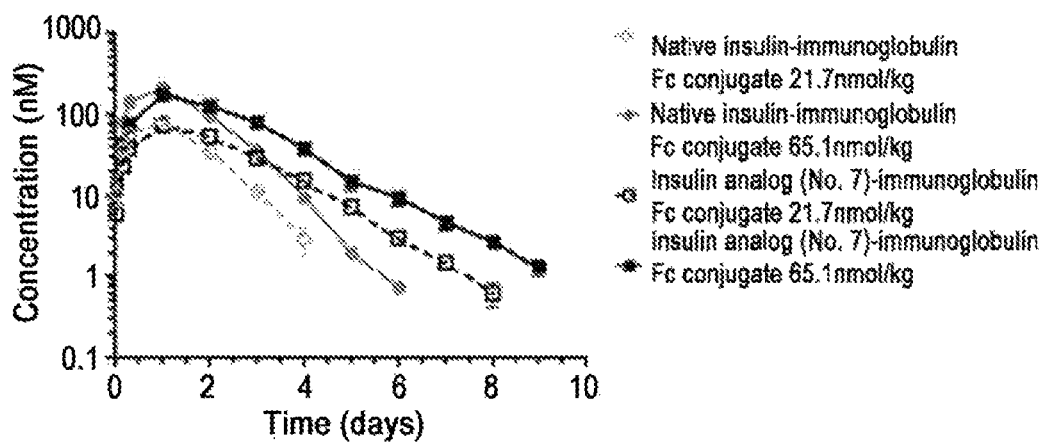
(B)
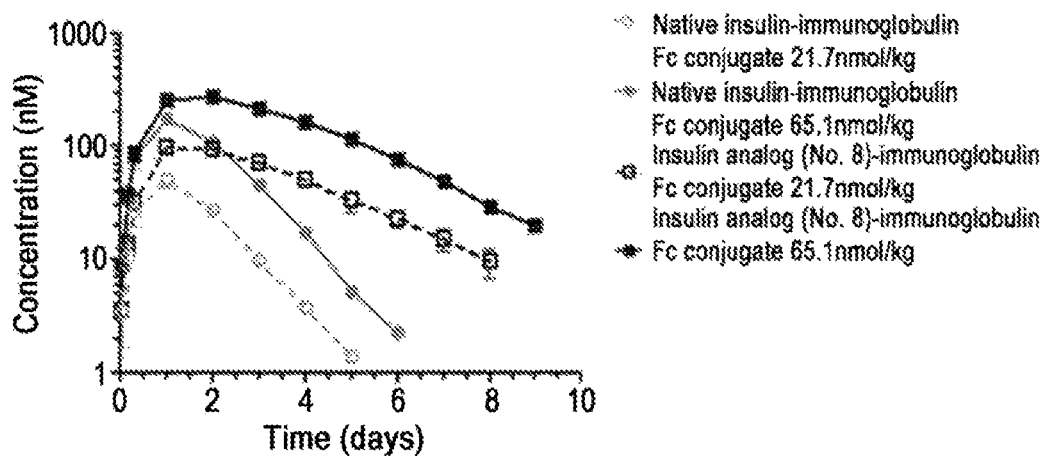
(C)
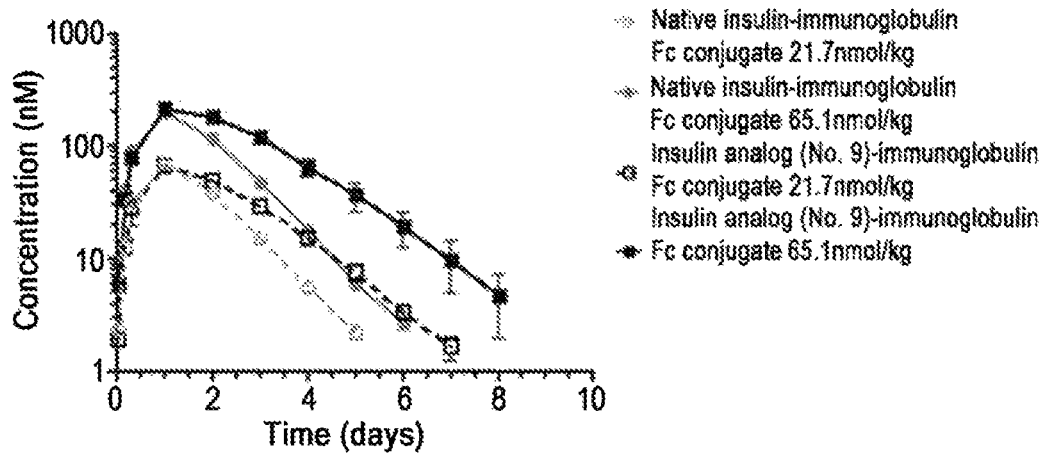

SEQUENCE LISTING

```
<160> NUMBER OF SEQ ID NOS: 40

<210> SEQ ID NO 1
<211> LENGTH: 39
<212> TYPE: DNA
<213> ORGANISM: Artificial Sequence
<220> FEATURE:
```

<223> OTHER INFORMATION: Primer

<400> SEQUENCE: 1
gggtccctgc agaagcgtgc gattgtggaa caatgctgt                                   39

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
acagcattgt tccacaatcg cacgcttctg cagggaccc                                   39

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
tccctgcaga agcgtggcgc ggtggaacaa tgctgtacc                                   39

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
ggtacagcat tgttccaccg cgccacgctt ctgcaggga                                   39

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
ctctaccagc tggaaaacgc gtgtaactga ggatcc                                      36

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
ggatcctcag ttacacgcgt tttccagctg gtagag                                      36

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
gttaaccaac acttgtgtgc gtcacacctg gtggaagct                                   39

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
agcttccacc aggtgtgacg cacacaagtg ttggttaac                              39

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
ctagtgtgcg gggaacgagc gttcttctac acacccaag                              39

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
cttgggtgtg tagaagaacg ctcgttcccc gcacactag                              39

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
gtgtgcgggg aacgaggcgc gttctacaca cccaagacc                              39

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
ggtcttgggt gtgtagaacg cgcctcgttc cccgcacac                              39

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
tgcggggaac gaggcttcgc gtacacaccc aagacccgc                              39

<210> SEQ ID NO 14
<211> LENGTH: 39
<212> TYPE: DNA
<213> ORGANISM: Artificial Sequence
<220> FEATURE:
<223> OTHER INFORMATION: Primer -continued

<400> SEQUENCE: 14
gcgggtcttg ggtgtgtacg cgaagcctcg ttccccgca                              39

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
ccagcatctg ctccctcgaa cagctggaga actactg                               37

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
cagtagttct ccagctgttc gagggagcag atgctgg                               37

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
cagcatctgc tccctcaacc agctggagaa ctac                                  34

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
gtagttctcc agctggttga gggagcagat gctg                                  34

<210> SEQ ID NO 19
<211> LENGTH: 258
<212> TYPE: DNA
<213> ORGANISM: Artificial Sequence
<220> FEATURE:
<223> OTHER INFORMATION: Analog 1

<400> SEQUENCE: 19
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtgcgat tgtggaacaa tgctgtacca gcatctgctc cctctaccag     240
ctggagaact actgcaac                                                  258

<210> SEQ ID NO 20
<211> LENGTH: 86
<212> TYPE: PRT
<213> ORGANISM: Artificial Sequence
<220> FEATURE:
<223> OTHER INFORMATION: Analog 1

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Ala Ile Val Glu Gln Cys Cys Thr Ser Ile Cys Ser Leu Tyr Gln
65                  70                  75                  80

Leu Glu Asn Tyr Cys Asn
                85

<210> SEQ ID NO 21
<211> LENGTH: 258
<212> TYPE: DNA
<213> ORGANISM: Artificial Sequence
<220> FEATURE:
<223> OTHER INFORMATION: Analog 2

<400> SEQUENCE: 21

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcgc ggtggaacaa tgctgtacca gcatctgctc cctctaccag     240
ctggagaact actgcaac                                                   258
```

<210> SEQ ID NO 22
<211> LENGTH: 86
<212> TYPE: PRT
<213> ORGANISM: Artificial Sequence
<220> FEATURE:
<223> OTHER INFORMATION: Analog 2

<400> SEQUENCE: 22

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ala Val Glu Gln Cys Cys Thr Ser Ile Cys Ser Leu Tyr Gln
65                  70                  75                  80

Leu Glu Asn Tyr Cys Asn
                85

<210> SEQ ID NO 23
<211> LENGTH: 258
<212> TYPE: DNA
<213> ORGANISM: Artificial Sequence
<220> FEATURE:
<223> OTHER INFORMATION: Analog 3

<400> SEQUENCE: 23

```
ttcgttaacc aacacttgtg tggctcacac ctggtggaag ctctctacct agtgtgcggg      60
gaacgaggct tcttctacac acccaagacc cgccggagg cagaggacct gcaggtgggg      120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaacg cgtgcaac                                                   258
```

```
<210> SEQ ID NO 24
<211> LENGTH: 86
<212> TYPE: PRT
<213> ORGANISM: Artificial Sequence
<220> FEATURE:
<223> OTHER INFORMATION: Analog 3

<400> SEQUENCE: 24
```

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ile Val Glu Gln Cys Cys Thr Ser Ile Cys Ser Leu Tyr Gln
 65                  70                  75                  80

Leu Glu Asn Ala Cys Asn
                 85

```
<210> SEQ ID NO 25
<211> LENGTH: 258
<212> TYPE: DNA
<213> ORGANISM: Artificial Sequence
<220> FEATURE:
<223> OTHER INFORMATION: Analog 4

<400> SEQUENCE: 25
```

```
ttcgttaacc aacacttgtg tgcgtcacac ctggtggaag ctctctacct agtgtgcggg      60
gaacgaggct tcttctacac acccaagacc cgccggagg cagaggacct gcaggtgggg      120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258
```

```
<210> SEQ ID NO 26
<211> LENGTH: 86
<212> TYPE: PRT
<213> ORGANISM: Artificial Sequence
<220> FEATURE:
<223> OTHER INFORMATION: Analog 4

<400> SEQUENCE: 26
```

Phe Val Asn Gln His Leu Cys Ala Ser His Leu Val Glu Ala Leu Tyr
 1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

```
Arg Gly Ile Val Glu Gln Cys Cys Thr Ser Ile Cys Ser Leu Tyr Gln
 65                  70                  75                  80

Leu Glu Asn Tyr Cys Asn
                85
```

<210> SEQ ID NO 27
<211> LENGTH: 258
<212> TYPE: DNA
<213> ORGANISM: Artificial Sequence
<220> FEATURE:
<223> OTHER INFORMATION: Analog 5

<400> SEQUENCE: 27

```
ttcgttaacc aacacttgtg tggctcacac ctggtggaag ctctctacct agtgtgcggg    60
gaacgagcgt tcttctacac acccaagacc cgccggagg cagaggacct gcaggtgggg   120
caggtggagc tgggcggggg ccctggtgca ggcagcctgc agcccttggc cctggagggg   180
tccctgcaga agcgtggcat tgtgaacaa tgctgtacca gcatctgctc cctctaccag   240
ctggagaact actgcaac                                                 258
```

<210> SEQ ID NO 28
<211> LENGTH: 86
<212> TYPE: PRT
<213> ORGANISM: Artificial Sequence
<220> FEATURE:
<223> OTHER INFORMATION: Analog 5

<400> SEQUENCE: 28

```
Phe Val Asn Gln His Leu Cys Gly Ser His Leu Val Glu Ala Leu Tyr
  1               5                  10                  15

Leu Val Cys Gly Glu Arg Ala Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ile Val Glu Gln Cys Cys Thr Ser Ile Cys Ser Leu Tyr Gln
 65                  70                  75                  80

Leu Glu Asn Tyr Cys Asn
                85
```

<210> SEQ ID NO 29
<211> LENGTH: 258
<212> TYPE: DNA
<213> ORGANISM: Artificial Sequence
<220> FEATURE:
<223> OTHER INFORMATION: Analog 6

<400> SEQUENCE: 29

```
ttcgttaacc aacacttgtg tggctcacac ctggtggaag ctctctacct agtgtgcggg    60
gaacgaggcg cgttctacac acccaagacc cgccgggagg cagaggacct gcaggtgggg   120
caggtggagc tgggcggggg ccctggtgca ggcagcctgc agcccttggc cctggagggg   180
tccctgcaga agcgtggcat tgtgaacaa tgctgtacca gcatctgctc cctctaccag   240
ctggagaact actgcaac                                                 258
```

<210> SEQ ID NO 30
<211> LENGTH: 86
<212> TYPE: PRT

<213> ORGANISM: Artificial Sequence
<220> FEATURE:
<223> OTHER INFORMATION: Analog 6

<400> SEQUENCE: 30

Phe Val Asn Gln His Leu Cys Gly Ser His Leu Val Glu Ala Leu Tyr
1               5                   10                  15
Leu Val Cys Gly Glu Arg Gly Ala Phe Tyr Thr Pro Lys Thr Arg Arg
            20                  25                  30
Glu Ala Glu Asp Leu Gln Val Gly Gln Val Glu Leu Gly Gly Gly Pro
        35                  40                  45
Gly Ala Gly Ser Leu Gln Pro Leu Ala Leu Glu Gly Ser Leu Gln Lys
    50                  55                  60
Arg Gly Ile Val Glu Gln Cys Cys Thr Ser Ile Cys Ser Leu Tyr Gln
65                  70                  75                  80
Leu Glu Asn Tyr Cys Asn
                85

<210> SEQ ID NO 31
<211> LENGTH: 258
<212> TYPE: DNA
<213> ORGANISM: Artificial Sequence
<220> FEATURE:
<223> OTHER INFORMATION: Analog 7

<400> SEQUENCE: 31
ttcgttaacc aaacacttgtg tggctcacac ctggtggaag ctctctacct agtgtgcggg      60
gaacgaggct tcgcgtacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258

<210> SEQ ID NO 32
<211> LENGTH: 86
<212> TYPE: PRT
<213> ORGANISM: Artificial Sequence
<220> FEATURE:
<223> OTHER INFORMATION: Analog 7

<400> SEQUENCE: 32

Phe Val Asn Gln His Leu Cys Gly Ser His Leu Val Glu Ala Leu Tyr
1               5                   10                  15
Leu Val Cys Gly Glu Arg Gly Phe Ala Tyr Thr Pro Lys Thr Arg Arg
            20                  25                  30
Glu Ala Glu Asp Leu Gln Val Gly Gln Val Glu Leu Gly Gly Gly Pro
        35                  40                  45
Gly Ala Gly Ser Leu Gln Pro Leu Ala Leu Glu Gly Ser Leu Gln Lys
    50                  55                  60
Arg Gly Ile Val Glu Gln Cys Cys Thr Ser Ile Cys Ser Leu Tyr Gln
65                  70                  75                  80
Leu Glu Asn Tyr Cys Asn
                85

<210> SEQ ID NO 33
<211> LENGTH: 261
<212> TYPE: DNA
<213> ORGANISM: Artificial Sequence
<220> FEATURE:
<223> OTHER INFORMATION: Analog 8

<400> SEQUENCE: 33

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctcgaacag     240
ctggagaact actgcaactg a                                              261
```

<210> SEQ ID NO 34
<211> LENGTH: 86
<212> TYPE: PRT
<213> ORGANISM: Artificial Sequence
<220> FEATURE:
<223> OTHER INFORMATION: Analog 8

<400> SEQUENCE: 34

```
Phe Val Asn Gln His Leu Cys Gly Ser His Leu Val Glu Ala Leu Tyr
 1               5                  10                  15
Leu Val Cys Gly Glu Arg Gly Phe Phe Tyr Thr Pro Lys Thr Arg Arg
                20                  25                  30
Glu Ala Glu Asp Leu Gln Val Gly Gln Val Glu Leu Gly Gly Gly Pro
            35                  40                  45
Gly Ala Gly Ser Leu Gln Pro Leu Ala Leu Glu Gly Ser Leu Gln Lys
        50                  55                  60
Arg Gly Ile Val Glu Gln Cys Cys Thr Ser Ile Cys Ser Leu Glu Gln
65                  70                  75                  80
Leu Glu Asn Tyr Cys Asn
                85
```

<210> SEQ ID NO 35
<211> LENGTH: 261
<212> TYPE: DNA
<213> ORGANISM: Artificial Sequence
<220> FEATURE:
<223> OTHER INFORMATION: Analog 9

<400> SEQUENCE: 35

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctcaaccag     240
ctggagaact actgcaactg a                                              261
```

<210> SEQ ID NO 36
<211> LENGTH: 86
<212> TYPE: PRT
<213> ORGANISM: Artificial Sequence
<220> FEATURE:
<223> OTHER INFORMATION: Analog 9

<400> SEQUENCE: 36

```
Phe Val Asn Gln His Leu Cys Gly Ser His Leu Val Glu Ala Leu Tyr
 1               5                  10                  15
Leu Val Cys Gly Glu Arg Gly Phe Phe Tyr Thr Pro Lys Thr Arg Arg
                20                  25                  30
Glu Ala Glu Asp Leu Gln Val Gly Gln Val Glu Leu Gly Gly Gly Pro
            35                  40                  45
```

```
Gly Ala Gly Ser Leu Gln Pro Leu Ala Leu Glu Gly Ser Leu Gln Lys
         50                  55                  60

Arg Gly Ile Val Glu Gln Cys Cys Thr Ser Ile Cys Ser Leu Asn Gln
 65                  70                  75                  80

Leu Glu Asn Tyr Cys Asn
             85

<210> SEQ ID NO 37
<211> LENGTH: 21
<212> TYPE: PRT
<213> ORGANISM: Artificial Sequence
<220> FEATURE:
<223> OTHER INFORMATION: A chain of Insulin Analogue
<220> FEATURE:
<221> NAME/KEY: VARIANT
<222> LOCATION: 1
<223> OTHER INFORMATION: Xaa = Gly or Ala
<220> FEATURE:
<221> NAME/KEY: VARIANT
<222> LOCATION: 2
<223> OTHER INFORMATION: Xaa = Ile or Ala
<220> FEATURE:
<221> NAME/KEY: VARIANT
<222> LOCATION: 14
<223> OTHER INFORMATION: Xaa = Tyr, Glu, or Asn
<220> FEATURE:
<221> NAME/KEY: VARIANT
<222> LOCATION: 19
<223> OTHER INFORMATION: Xaa = Tyr or Ala

<400> SEQUENCE: 37

Xaa Xaa Val Glu Gln Cys Cys Thr Ser Ile Cys Ser Leu Xaa Gln Leu
  1               5                  10                  15

Glu Asn Xaa Cys Asn
             20

<210> SEQ ID NO 38
<211> LENGTH: 30
<212> TYPE: PRT
<213> ORGANISM: Artificial Sequence
<220> FEATURE:
<223> OTHER INFORMATION: B chain of Insulin Analogue
<220> FEATURE:
<221> NAME/KEY: VARIANT
<222> LOCATION: 8
<223> OTHER INFORMATION: Xaa = Gly or Ala
<220> FEATURE:
<221> NAME/KEY: VARIANT
<222> LOCATION: 23
<223> OTHER INFORMATION: Xaa = Gly or Ala
<220> FEATURE:
<221> NAME/KEY: VARIANT
<222> LOCATION: 24
<223> OTHER INFORMATION: Xaa = Phe or Ala
<220> FEATURE:
<221> NAME/KEY: VARIANT
<222> LOCATION: 25
<223> OTHER INFORMATION: Xaa = Phe or Ala

<400> SEQUENCE: 38

Phe Val Asn Gln His Leu Cys Xaa Ser His Leu Val Glu Ala Leu Tyr
  1               5                  10                  15

Leu Val Cys Gly Glu Arg Xaa Xaa Xaa Tyr Thr Pro Lys Thr
             20                  25                  30

<210> SEQ ID NO 39
<211> LENGTH: 21
<212> TYPE: PRT
<213> ORGANISM: Artificial Sequence
```

```
<220> FEATURE:
<223> OTHER INFORMATION: A chain of Insulin

<400> SEQUENCE: 39

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 40
<211> LENGTH: 30
<212> TYPE: PRT
<213> ORGANISM: Artificial Sequence
<220> FEATURE:
<223> OTHER INFORMATION: B chain of Insulin

<400> SEQUENCE: 40

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

LONG-ACTING INSULIN AND USE THEREOF

CROSS REFERENCE TO RELATED APPLICATIONS

This application is a National Phase application under 35 U.S.C. § 371 of International Application No. PCT/KR2015/000576 filed Jan. 20, 2015, which claims priority benefit to KR Application No. 10-2014-0006938 filed Jan. 20, 2014, the disclosures of each of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 768502000100SEQLIST.txt, date recorded: Oct. 14, 2016, size: 17 KB).

TECHNICAL FIELD

The present invention relates to an insulin analog that has reduced insulin receptor binding affinity for the purpose of increasing the blood half-life of insulin, and long-acting insulin using the same.

BACKGROUND ART

Generally, insulin is a hormone secreted by the pancreas of the human body, which regulates blood glucose levels, and plays a role in maintaining normal blood glucose levels while carrying surplus glucose in the blood to cells to provide energy for cells. In diabetic patients, however, insulin does not function properly due to lack of insulin, resistance to insulin, and loss of beta-cell function, and thus glucose in the blood cannot be utilized as an energy source and the blood glucose level is elevated, leading to hyperglycemia. Eventually, urinary excretion occurs, contributing to development of various complications. Therefore, insulin therapy is essential for patients with abnormal insulin secretion (Type I) or insulin resistance (Type II), and blood glucose levels can be normally regulated by insulin administration. However, like other protein and peptide hormones, insulin has a very short in-vivo half-life, and thus has a disadvantage of repeated administration. Such frequent administration causes severe pain and discomfort for the patients. For this reason, in order to improve quality of life by increasing an in-vivo half-life of the protein and reducing the administration frequency, many studies on protein formulation and chemical conjugation (fatty acid conjugate, polyethylene polymer conjugate) have been conducted. Commercially available long-acting insulin includes insulin glargine manufactured by Sanofi Aventis (lantus, lasting for about 20 hours to 22 hours), and insulin detemir (levemir, lasting for about 18 hours to 22 hours) and tresiba (degludec, lasting for about 40 hours) manufactured by Novo Nordisk. These long-acting insulin formulations produce no peak in the blood insulin concentration, and thus they are suitable as basal insulin. However, because these formulations do not have a sufficiently long half-life, the disadvantage of one or two injections per day still remains. Accordingly, there is a limitation in achieving the intended goal that administration frequency is remarkably reduced to improve convenience of diabetic patients in need of long-term administration.

Authier F et al. (Biochem J. 1998 Jun. 1; 332 (Pt 2): 421-30), Duckworth W C et al. (Endocr Rev. 1998 October; 19(5): 608-24) and Valera Mora M E et al. (J Am Coll Nutr. 2003 December; 22(6): 487-93), etc., have reported in-vivo insulin clearance processes. According to the reports, 50% or more of insulin is removed in the kidney and the rest is removed via a receptor mediated clearance (RMC) process in target sites such as muscle, fat, liver, etc.

In this regard, Lin S et al. (J Pharmacol Exp Ther, 1998, 286(2): 959-66), Brange J et al. (Diabetes Care. 1990 September; 13(9): 923-54), and Ribel U et al. (Diabetes, 1990, 39: 1033-9), etc., have reported that in-vitro activity is reduced to avoid RMC of insulin, thereby increasing the insulin level in the blood.

Under these circumstances, the present inventors have made many efforts to increase the blood half-life of insulin. As a result, they have discovered an insulin analog that has reduced insulin receptor binding affinity, and also confirmed that a formulation containing the same, which is capable of increasing the half-life, bioavailability, and maintaining sustained activity of insulin, can also increase the blood half-life of insulin, thereby completing the present invention.

DISCLOSURE

Technical Problem

An object of the present invention is to provide a novel insulin analog that has reduced insulin receptor binding affinity for the purpose of prolonging an in-vivo half-life of insulin, and a long-acting formulation thereof.

Specifically, an object of the present invention is to provide an insulin analog having reduced insulin receptor binding affinity, compared to native insulin.

Another object of the present invention is to provide a polynucleotide encoding the insulin analog, an expression vector including the polynucleotide, and a transformant including the expression vector.

Still another object of the present invention is to provide long-acting insulin, in which a biocompatible material capable of prolonging a half-life is linked to an insulin analog.

Still another object of the present invention is to provide a method for long-acting insulin including (a) preparing (i) an insulin analog, and (ii) a biocompatible material selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer, respectively; and (b) linking the insulin analog to a biocompatible material.

Still another object of the present invention is to provide a conjugate of Chemical Formula 1 below.

$$X-La-F; \quad \text{[Chemical Formula 1]}$$

wherein X is an insulin analog having reduced insulin receptor binding affinity compared to the native insulin, L is a linker, a is 0 or a natural number, with the proviso that each L is independent from each other when a is 2 or higher, and F is a material capable of increasing the in-vivo half-life of an insulin analog.

Still another object of the present invention is to provide a long-acting insulin formulation including the conjugate, with improved in-vivo duration and stability.

Still another object of the present invention is to provide a long-acting formulation including the conjugate, for the treatment of diabetes.

Still another object of the present invention is to provide a method for treating insulin-related diseases, including administering the insulin analog or the insulin analog conjugate to a subject in need thereof.

Technical Solution

In order to accomplish the above objects, in an aspect, the present invention provides an insulin analog having reduced insulin receptor binding affinity compared to the native insulin.

In an exemplary embodiment of the present invention, the insulin analog has an increased half-life of 10% or higher, compared to the native insulin.

In another exemplary embodiment of the present invention, the insulin analog has a mutation or deletion in at least one amino acid of the native insulin.

In still another exemplary embodiment of the present invention, the insulin analog is characterized in that one or more amino acids at positions 1 to 3, 5, 8, 10, 12, 16, and 23 to 30 of the B chain of insulin, and at positions 1, 2, 5, 8, 10, 12, 14, 16 to 19, and 21 of the A chain of insulin are substituted with other amino acid(s), or deleted.

In still another exemplary embodiment of the present invention, the insulin analog is characterized in that one or more amino acids at positions 8 and 23 to 25 of the B chain of insulin, and at positions 1, 2, 14, and 19 of the A chain of insulin are substituted with other amino acid(s).

In still another exemplary embodiment of the present invention, the substituting amino acid is selected from the group consisting of alanine, glutamic acid, asparagine, isoleucine, valine, glutamine, glycine, lysine, histidine, cysteine, phenylalanine, tryptophan, proline, serine, threonine, and aspartic acid.

In still another exemplary embodiment of the present invention, the insulin analog has reduced insulin receptor binding affinity due to the deletion in at least one amino acid of the A chain or the B chain of the native insulin.

In still another exemplary embodiment of the present invention, the insulin analog includes the A chain of SEQ ID NO: 37 represented by Formula 1 below and the B chain of SEQ ID NO: 38 represented by Formula 2 below:

[Formula 1]
(SEQ ID NO: 37)
Xaa1-Xaa2-Val-Glu-Gln-Cys-Cys-Thr-Ser-Ile-Cys-Ser-

Leu-Xaa3-Gln-Leu-Glu-Asn-Xaa4-Cys-Asn

In Formula 1 above,
Xaa1 is glycine or alanine,
Xaa2 is isoleucine or alanine,
Xaa3 is tyrosine, glutamic acid, or asparagine, and
Xaa4 is tyrosine or alanine.

[Formula 2]
(SEQ ID NO: 38)
Phe-Val-Asn-Gln-His-Leu-Cys-Xaa5-Ser-His-Leu-Val-

Glu-Ala-Leu-Tyr-Leu-Val-Cys-Gly-Glu-Arg-Xaa6-Xaa7-

Xaa8-Tyr-Thr-Pro-Lys-Thr

In Formula 2 above,
Xaa5 is glycine or alanine,
Xaa6 is glycine or alanine,
Xaa7 is phenylalanine or alanine, and
Xaa8 is phenylalanine or alanine.

In still another exemplary embodiment of the present invention, the insulin analog includes:
(i) the A chain, wherein, in Formula 1, Xaa1 is alanine, Xaa2 is isoleucine, Xaa3 is tyrosine, and Xaa4 is tyrosine; and the B chain, wherein, in Formula 2, Xaa5 is glycine, Xaa6 is glycine, Xaa7 is phenylalanine, and Xaa8 is phenylalanine;
(ii) the A chain, wherein, in Formula 1, Xaa1 is glycine, Xaa2 is alanine, Xaa3 is tyrosine, and Xaa4 is tyrosine; and the B chain, wherein, in Formula 2, Xaa5 is glycine, Xaa6 is glycine, Xaa7 is phenylalanine, and Xaa8 is phenylalanine;
(iii) the A chain, wherein, in Formula 1, Xaa1 is glycine, Xaa2 is isoleucine, Xaa3 is glutamic acid or asparagine, and Xaa4 is tyrosine; and the B chain, wherein, in Formula 2, Xaa5 is glycine, Xaa6 is glycine, Xaa7 is phenylalanine, and Xaa8 is phenylalanine;
(iv) the A chain, wherein, in Formula 1, Xaa1 is glycine, Xaa2 is isoleucine, Xaa3 is tyrosine, and Xaa4 is alanine; and the B chain, wherein, in Formula 2, Xaa5 is glycine, Xaa6 is glycine, Xaa7 is phenylalanine, and Xaa8 is phenylalanine;
(v) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is alanine, Xaa6 is glycine, Xaa7 is phenylalanine, and Xaa8 is phenylalanine;
(vi) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is glycine, Xaa6 is alanine, Xaa7 is phenylalanine, and Xaa8 is phenylalanine;
(vii) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is glycine, Xaa6 is glycine, Xaa7 is alanine, and Xaa8 is phenylalanine; or
(viii) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is glycine, Xaa6 is glycine, Xaa7 is phenylalanine, and Xaa8 is alanine.

In another aspect, the present invention provides a polynucleotide encoding the insulin analog, an expression vector including the polynucleotide, and a transformant including the expression vector.

In still another aspect, the present invention provides long-acting insulin, in which a biocompatible material capable of prolonging a half-life is linked to the insulin analog.

In an exemplary embodiment of the present invention, the biocompatible material is selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer.

In another exemplary embodiment of the present invention, the insulin analog and the biocompatible material are linked to each other by a peptide bond.

In still another exemplary embodiment of the present invention, the insulin analog and the biocompatible material are linked by a linker selected from the group consisting of polyethylene glycol, fatty acid, saccharide, a polymer, a low molecular weight compound, a nucleotide, and a combination thereof.

In still another exemplary embodiment of the present invention, the insulin analog and the biocompatible material are linked by a linker interposed therebetween, and the biocompatible material is an FcRn-binding material, wherein the linker is a peptide linker, or a non-peptide linker selected from the group consisting of polyethylene glycol, polypropylene glycol, copolymers of ethylene glycol-propylene glycol, polyoxytheylated polyols, polyvinyl alcohols, polysaccharides, dextran, polyvinyl ether, biodegradable polymers, lipid polymers, chitins, hyaluronic acid, and a combination thereof.

In still another exemplary embodiment of the present invention, the FcRn-binding material is a polypeptide including an immunoglobulin Fc region.

In still another exemplary embodiment of the present invention, each end of the non-peptide linker is respectively linked to an amine group or thiol group of the biocompatible material and the insulin analog.

In still another aspect, the present invention provides a method for preparing long-acting insulin, including:
(a) preparing (i) an insulin analog; and (ii) a biocompatible material selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer, respectively; and
(b) linking the insulin analog to the biocompatible material.

In still another aspect, the present invention provides a conjugate of Chemical Formula 1 below:

X—La—F;     [Chemical Formula 1]

wherein X is an insulin analog having reduced insulin receptor binding affinity compared to the native insulin,
L is a linker,
a is 0 or a natural number, with the proviso that each L is independent from each other when a is 2 or higher, and
F is a material capable of increasing the in-vivo half-life of an insulin analog.

In an exemplary embodiment of the present invention, X is an insulin analog having reduced insulin receptor binding affinity compared to the native insulin, wherein the insulin analog has a mutation or deletion in at least one amino acid of the A chain or the B chain of the insulin.

In another exemplary embodiment of the present invention, the insulin analog is characterized in that one or more amino acids at positions 1 to 3, 5, 8, 10, 12, 16, and 23 to 30 of the B chain of insulin, and at positions 1, 2, 5, 8, 10, 12, 14, 16 to 19, and 21 of the A chain of insulin are substituted with other amino acid(s), or deleted.

In still another exemplary embodiment of the present invention, the insulin analog is characterized in that one or more amino acids at positions 8 and 23 to 25 of the B chain of insulin, and at positions 1, 2, 14, and 19 of the A chain of insulin are substituted with other amino acid(s).

In still another exemplary embodiment of the present invention, the substituting amino acid is selected from the group consisting of alanine, glutamic acid, asparagine, isoleucine, valine, glutamine, glycine, lysine, histidine, cysteine, phenylalanine, tryptophan, proline, serine, threonine, and aspartic acid.

In still another exemplary embodiment of the present invention, the material capable of increasing the in-vivo half-life of the insulin analog is elected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue, a nucleotide, fibronectin, transferrin, saccharide, and a polymer.

In still another exemplary embodiment of the present invention, L is selected from the group consisting of a peptide, polyethylene glycol, fatty acid, saccharide, a polymer, a low molecular weight compound, a nucleotide, and a combination thereof.

In still another exemplary embodiment of the present invention, X and F are linked by L through a covalent chemical bond, a non-covalent chemical bond, or a combination thereof.

In still another exemplary embodiment of the present invention, the polymer is a non-peptide linker selected from the group consisting of polypropylene glycol, copolymers of ethylene glycol-propylene glycol, polyoxytheylated polyol, polyvinyl alcohols, polysaccharides, dextran, polyvinyl ether, biodegradable polymers, lipid polymers, chitins, hyaluronic acid, oligonucleotides, and a combination thereof.

In still another exemplary embodiment of the present invention, F is an IgG Fc region.

In still another aspect, the present invention provides a long-acting insulin formulation, including the conjugate for the treatment of diabetes, with improved in-vivo duration and stability.

In still another aspect, the present invention provides a method for the treatment of insulin-related diseases including administering the insulin analog or the insulin analog conjugate to a subject in need thereof, Advantageous Effects The long-acting insulin of the present invention has a markedly increased half-life in the blood compared to the native insulin, and thus, the long-acting insulin of the present invention can improve convenience for patients in need of insulin administration.

DESCRIPTION OF DRAWINGS

FIG. 1 shows the result of purity analysis of an insulin analog by protein electrophoresis, which is the result of the representative insulin analog, Analog No. 7 (Lane 1: size marker, Lane 2: native insulin, and Lane 3: insulin analog (No. 7)).

FIG. 2 shows the result of purity analysis of an insulin analog by high pressure chromatography, which is the result of the representative insulin analog, Analog No. 7 ((A) RP-HPLC, (B) SE-HPLC).

FIG. 3 shows the result of peptide mapping of an insulin analog, which is the result of the representative insulin analog, Analog No. 7 ((A) native insulin: A chain (SEQ ID NO: 39), B chain (SEQ ID NO: 40), (B) insulin analog (No. 7): A chain (residues 66-86 of SEQ ID NO: 32), B chain (residues 1-30 of SEQ ID NO: 32)).

FIG. 4 shows the result of purity analysis of an insulin analog-immunoglobulin Fc conjugate by protein electrophoresis, which is the result of the representative insulin analog, Analog No. 7 (Lane 1: size marker, Lane 2: insulin analog (No. 7)-immunoglobulin Fc conjugate).

FIG. 5 shows the result of purity analysis of an insulin analog-immunoglobulin Fc conjugate by high pressure chromatography, which is the result of the representative insulin analog, Analog No. 7 ((A) RP-HPLC, (B) SE-HPLC, and (C) IE-HPLC).

FIG. 6 shows the result of pharmacokinetics analysis of native insulin-immunoglobulin Fc conjugate and insulin analog-immunoglobulin Fc conjugate in normal rats. ((A) native insulin-immunoglobulin Fc conjugate and insulin analog (No. 7)-immunoglobulin Fc conjugate, (B) native insulin-immunoglobulin Fc conjugate and insulin analog (No. 8)-immunoglobulin Fc conjugate, and (C) native insulin-immunoglobulin Fc conjugate and insulin analog (No. 9)-immunoglobulin Fc conjugate). (○: native insulin-immunoglobulin Fc conjugate (21.7 nmol/kg), ●: native insulin-immunoglobulin Fc conjugate (65.1 nmol/kg), □: insulin analog-immunoglobulin Fc conjugate (21.7 nmol/kg), ■: insulin analog-immunoglobulin Fc conjugate (65.1 nmol/kg)).

BEST MODE

In order to achieve the present invention, in an aspect, there is provided an insulin analog having reduced insulin receptor binding affinity, compared to the native insulin.

As used herein, the term "insulin analog" refers to a material, which possesses the function of controlling an in-vivo blood glucose level identical to that of native insulin. For the purpose of the present invention, the insulin analog is preferably a material having reduced insulin receptor binding affinity, compared to the native insulin. Additionally, the insulin analog may be one, which has an increased half-life of 10% or higher than the native insulin due to the reduced insulin receptor binding affinity, but is not limited thereto.

Specifically, the insulin analog may be an insulin analog having reduced insulin receptor binding affinity, compared to the native insulin, in which an amino acid of the B chain or the A chain of the insulin is mutated or deleted. For example, the insulin analog may be one having reduced insulin receptor binding affinity compared to the native insulin, via modification of part of the amino acid(s) of the native insulin in the form of addition, deletion, or substitution.

Meanwhile, native insulin is a hormone secreted by the pancreas, which generally serves to promote intracellular absorption of glucose and inhibit lipolysis, thereby controlling the in-vivo blood glucose level. Insulin in the form of proinsulin, which is a precursor without the capability of controlling blood glucose level, is convered via a process to insulin, which has the capability of controlling blood glucose level. Insulin has two polypeptide chains, i.e., the A chain having 21 amino acid residues and the B chain having 30 amino acid residues, and they are linked together by two disulfide bonds. Each of the A chain and the B chain of native insulin may include the amino acid sequence represented by SEQ ID NOS: 39 and 40, respectively.

A chain:
(SEQ ID NO: 39)
Gly-Ile-Val-Glu-Gln-Cys-Cys-Thr-Ser-Ile-Cys-Ser-

Leu-Tyr-Gln-Leu-Glu-Asn-Tyr-Cys-Asn

B chain:
(SEQ ID NO: 40)
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The insulin analogs used in Examples of the present invention are those prepared by genetic recombination technique. However, the insulin analogs of the present invention are not limited thereto, but may include all insulins having reduced insulin receptor binding affinity.

Specifically, the insulin analogs may include inverted insulins, insulin variants, insulin fragments, insulin agonists, insulin derivatives, etc., and the preparation method may include a solid phase method as well as genetic recombination technique, but is not limited thereto.

The insulin agonist refers to a substance which is bound to the in-vivo receptor of insulin to exhibit the biological activities of insulin, regardless of the structure of the insulin.

The insulin derivative includes a peptide form, which has a homology to the amino acid sequences of the A chain and the B chain of native insulin, respectively, and has some groups of amino acid residues altered in the form of chemical substitution (e.g., alpha-methylation, alpha-hydroxylation), removal (e.g., deamination), or modification (e.g., N-methylation), while having a function of controlling blood glucose in the body.

Additionally, the insulin derivative may also include a peptide mimic, and a low molecular weight compound or a polymer, which can control the in-vivo blood glucose level by being conjugated to an insulin receptor, even in the absence of a homology to the amino acid sequence of native insulin.

The insulin fragment refers to a form of insulin in which one or more amino acids are added to or deleted from insulin, and the added amino acid(s) may be those not present in nature (e.g., D-type amino acid), and this type of insulin fragment possesses the function of controlling the in-vivo blood glucose level.

The insulin variant refers to a peptide in which one or more amino acid sequences differ from those of insulin, and possesses the function of controlling the in-vivo blood glucose level.

The respective method for preparation of insulin agonists, derivatives, fragments, and variants of the present invention may be used independently or in combination. For example, peptides in which one or more amino acid sequences differ from those of insulin, and which have deamination at the N-terminal amino acid residue and also have the function of controlling the in-vivo blood glucose level are included in the scope of the present invention.

Specifically, the insulin analogs may be those in which one or more amino acids at positions 1 to 3, 5, 8, 10, 12, 16, and 23 to 30 of the B chain of insulin, and at positions 1, 2, 5, 8, 10, 12, 14, 16 to 19, and 21 of the A chain of insulin are substituted with other amino acid(s); or more specifically, may be an insulin analog, in which one or more amino acids at positions 8 and 23 to 25 of the B chain of insulin, and at positions 1, 2, 14, and 19 of the A chain of insulin are substituted with other amino acid(s). Specifically, the insulin analog may be an insulin analog, in which one or more amino acids, 2 or more amino acids, 3 or more amino acids, 4 or more amino acids, 5 or more amino acids, 6 or more amino acids, 7 or more amino acids, 8 or more amino acids, 9 or more amino acids, 10 or more amino acids, 11 or more amino acids, 12 or more amino acids, 13 or more amino acids, 14 or more amino acids, 15 or more amino acids, 16 or more amino acids, 17 or more amino acids, 18 or more amino acids, 19 or more amino acids, 20 or more amino acids, 21 or more amino acids, 22 or more amino acids, 23 or more amino acids, 24 or more amino acids, 25 or more amino acids, 26 or more amino acids, or 27 or more amino acids described above are substituted with other amino acids, but is not limited thereto.

The amino acid residues at positions described above may be substituted with alanine, glutamic acid, asparagine, isoleucine, valine, glutamine, glycine, lysine, histidine, cysteine, phenylalanine, tryptophan, proline, serine, threonine, and/or aspartic acid. Additionally, insulin analogs having reduced insulin receptor binding affinity due to the deletion in one or more amino acids in the A chain or the B chain of insulin also belong to the scope of the present invention, but any insulin analog having reduced insulin receptor binding affinity may be included without limitation.

The insulin analogs according to the present invention include any peptide having reduced insulin receptor binding affinity compared to the native insulin due to the introduction of a substitution, an addition, or a modification after translation (e.g., methylation, acylation, ubiquitination, and intramolecular covalent bond) of an amino acid(s) in the amino acid sequences of the A chain and the B chain of native insulin. For substitution or addition of the amino acid(s), atypical or non-naturally occurring amino acids may be used, in addition to the 20 conventionally observed amino acids. The commercial origin of the atypical amino acids may include Sigma-Aldrich, ChemPep, and Genzymepharmaceuticals. The sequences of the peptides containing these amino acids and the typical peptides may be synthesized by or purchased from commercial peptide synthesizing companies, e.g., American peptide company, Bachem (USA) and Anygen (Korea).

More specifically, the insulin analogs may include the A chain of SEQ ID NO: 37 represented by Formula 1 below and the B chain of SEQ ID NO: 38 represented by Formula 2 below. Additionally, the insulin analogs may be in a form where the sequences of the A chain and the B chain are linked together by a disulfide bond, but are not limited thereto.

[Formula 1]
(SEQ ID NO: 37)
Xaa1-Xaa2-Val-Glu-Gln-Cys-Cys-Thr-Ser-Ile-Cys-Ser-

Leu-Xaa3-Gln-Leu-Glu-Asn-Xaa4-Cys-Asn

In Formula 1 above,
Xaa1 is glycine or alanine,
Xaa2 is isoleucine or alanine,
Xaa3 is tyrosine, glutamic acid, or asparagine, and
Xaa4 is tyrosine or alanine.

[Formula 2]
(SEQ ID NO: 38)
Phe-Val-Asn-Gln-His-Leu-Cys-Xaa5-Ser-His-Leu-Val-

Glu-Ala-Leu-Tyr-Leu-Val-Cys-Gly-Glu-Arg-Xaa6-Xaa7-

Xaa8-Tyr-Thr-Pro-Lys-Thr

In Formula 2 above,
Xaa5 is glycine or alanine,
Xaa6 is glycine or alanine,
Xaa7 is phenylalanine or alanine, and
Xaa8 is phenylalanine or alanine.
More specifically, the insulin analog may include:
(i) the A chain, wherein, in Formula 1, Xaa1 is alanine, Xaa2 is isoleucine, Xaa3 is tyrosine, and Xaa4 is tyrosine; and the B chain, wherein, in Formula 2, Xaa5 is glycine, Xaa6 is glycine, Xaa7 is phenylalanine, and Xaa8 is phenylalanine;
(ii) the A chain, wherein, in Formula 1, Xaa1 is glycine, Xaa2 is alanine, Xaa3 is tyrosine, and Xaa4 is tyrosine; and the B chain, wherein, in Formula 2, Xaa5 is glycine, Xaa6 is glycine, Xaa7 is phenylalanine, and Xaa8 is phenylalanine;
(iii) the A chain, wherein, in Formula 1, Xaa1 is glycine, Xaa2 is isoleucine, Xaa3 is glutamic acid or asparagine, and Xaa4 is tyrosine; and the B chain, wherein, in Formula 2, Xaa5 is glycine, Xaa6 is glycine, Xaa7 is phenylalanine, and Xaa8 is phenylalanine;
(iv) the A chain, wherein, in Formula 1, Xaa1 is glycine, Xaa2 is isoleucine, Xaa3 is tyrosine, and Xaa4 is alanine; and the B chain, wherein, in Formula 2, Xaa5 is glycine, Xaa6 is glycine, Xaa7 is phenylalanine, and Xaa8 is phenylalanine;
(v) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is alanine, Xaa6 is glycine, Xaa7 is phenylalanine, and Xaa8 is phenylalanine;
(vi) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is glycine, Xaa6 is alanine, Xaa7 is phenylalanine, and Xaa8 is phenylalanine;
(vii) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is glycine, Xaa6 is glycine, Xaa7 is alanine, and Xaa8 is phenylalanine; or
(viii) the A chain, wherein, in Formula 1, Xaa1 is glycine, Xaa2 is isoleucine, Xaa3 is tyrosine, and Xaa4 is tyrosine; and the B chain, wherein, in Formula 2, Xaa5 is glycine, Xaa6 is glycine, Xaa7 is phenylalanine, and Xaa8 is alanine, but is not limited thereto.

For example, those peptides which have a homology of 70% or higher, specifically 80% or higher, more specifically 90% or higher, and even more specifically 95% or higher to the sequence of the corresponding insulin analog, while including the characteristic amino acid residues described above, and have reduced insulin receptor binding affinity compared to the native insulin are included in the scope of the present invention.

As used herein, the term "homology" refers to a level of similarity with regard to the amino acid sequence of a wild type protein or a polynucleotide sequence encoding the same, and includes the sequences having a sequence with the above percentage or higher of the same sequence with the amino acid sequence or polynucleotide sequence of the present invention. This homology may be determined via comparison by the naked eye, or may be determined via a bioinformatic algorithm, which analyzes the degree of homology by arranging the two sequences. The homology between the two amino acid sequences may be indicated in percentage. Useful automated algorithms can be used at both GAP, BESTFIT, and FASTA of Wisconsin Genetics Software Package (Genetics Computer Group, Madison, Wis., USA) and TFASTA computer software module. The automated array algorithms include the sequence array algorithms of Needleman & Wunsch, Pearson & Lipman, and Smith & Waterman. The determination on algorithm and homology is automated in softwares including FASTP, BLAST, BLAST2, PSIBLAST, and CLUSTAL W.

In still another aspect of the present invention, there is provided a polynucleotide encoding the insulin analog, an expression vector including the polynucleotide, and a transformant including the expression vector.

The insulin analogs are the same as described above.

The polynucleotide is deoxyribonucleotide (DNA) or ribonucleotide (RNA) present in a single-stranded or double-stranded state, and means to include genomic DNA, cDNA, and RNA to be transcribed therefrom. The nucleotide, as a basic constitutional unit, not only includes natural nucleotides but also analogs in which a sugar or base region is modified (Scheit, Nucleotide Analogs, John Wiley, New York, 1980; Uhlman and Peyman, Chemical Reviews, 90: 543-584, 1990). The polynucleotide of the present invention may be separated or prepared by a standard molecular biology technique. For example, the polynucleotide may be amplified from a gene sequence of native insulin (NM_000207.2, NCBI) via polymerase chain reaction (PCR), and prepared by a standard synthesis technology using an automated DNA synthesizer. In the present invention, the term polynucleotide may be used interchangeably with nucleic acid.

The polynucleotide encoding the insulin analog may include the polynucleotide encoding the amino acid sequences of the A chain and the B chain described above, and the examples may include polynucleotides of SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, and SEQ ID NO: 35, but are not limited thereto. For example, those polynucleotides which have a homology of 70% or higher with the above sequences, specifically 80% or higher, more specifically 90% or higher, and even more specifically 95% or higher, in addition to the polynucleotides described above, while having reduced insulin receptor binding affinity compared to the native insulin, are also included in the scope of the present invention.

The recombinant vector according to the present invention may be constructed as a vector for typical cloning or for expression, and may be constructed as a vector for using a eukaryotic cell or prokaryotic cell as a host cell.

As used herein, the term "vector" refers to a nucleic acid construct, which, being a recombinant vector capable of expressing a target protein in a host cell, includes essential regulation factors that are operably linked so that a nucleic acid insert can be expressed. The present invention can prepare a recombinant vector including the nucleic acid encoding the regulation factors, and the insulin analogs of the present invention may be obtained via transformation or transfection of the recombinant vector into the host cell.

In the present invention, the nucleic acid encoding the insulin analogs is operably linked to the promoter. As used herein, the term "operatively linked" refers to a functional linkage between an expression-regulating sequence of nucleic acid (e.g., a promoter, a signal sequence, a ribosome-binding domain, a transcription termination sequence, etc.) and a sequence of a different nucleic acid, and the regulation sequence can control the transcription and/or translation of the sequence of the different nucleic acid by the linkage.

As used herein, the term "promoter" refers to a sequence of a non-translated nucleic acid upstream of a coding region, which includes a polymerase-binding domain and has a transcription initiation activity for a gene downstream of the promoter into mRNA, that is, a DNA domain to which a polymerase binds to initiate the transcription of a gene, and is located on the 5'-region of the initiation area of mRNA transcription.

For example, when the vector of the present invention is a recombinant vector and employs a procaryotic cell as a host cell, the vector generally includes a strong promoter (e.g., tac promoter, lac promoter, lacUV5 promoter, lpp promoter, pLλ promoter, pRλ promoter, rac5 promoter, amp promoter, recA promoter, SP6 promoter, trp promoter, T7 promoter, etc.) capable of executing the transcription, a ribosome-binding domain, and a sequence for transcription/translation termination sequence.

Additionally, the vector to be used in the present invention may be constructed by manipulating plasmids commonly used in the art (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phage (e.g., λgt4-λB, λ-Charon, λΔz1, M13, etc.), or viruses (e.g., SV40, etc.).

Additionally, the vector of the present invention is a recombinant vector and employs a eukaryotic cell as a host cell, the vector generally includes a promoter derived from a genome of a mammalian cell (e.g., metallothionein promoter) or a promoter derived from a mammalian virus (e.g., adenovirus late promoter, cowpox virus 7.5K promoter, SV40 promoter, cytomegalovirus promoter, and tk promoter of HSV) may be used, and has a polyadenylation sequence (e.g., bovine growth hormone terminator and SV40-dreived poly adenylation sequence) as a transcription termination sequence.

Additionally, the recombinant vector of the present invention is a selection marker and includes an antibiotic-resistant gene commonly used in the art, and for example, genes having resistance to ampicillin, gentamycin, carbenicillin, chloramphenicol, streptomycin, kanamycin, geneticin, neomycin, and tetracycline may be used.

The recombinant vector of the present invention may additionally include other sequences as necessary, in order to facilitate an easy purification of the target protein collected from the recombinant vector, i.e., the insulin analog.

The sequence to be additionally included in the vector may be a tag sequence for protein purificataion, e.g., glutathione S-transferase (Pharmacia, USA), a maltose-binding protein (NEB, USA), FLAG (IBI, USA), 6-histidine (hexa-histidine), etc., but the kinds of the sequences necessary for target protein purification are not limited thereto.

The fusion protein expressed by the recombinant vector including the tag sequence as described above may be purified via affinity chromatography. For example, when glutathione-S-transferase is fused, glutathione as a substrate for the enzyme may be used, whereas when 6-histidine tag is used a desired target protein may be easily collected via Ni-NTA column.

A transformant in which the vector is transformed may be constructed using the recombinant vector including a polynucleotide encoding the insulin analog.

As used herein, the term "transformation", in which DNA is introduced into a host cell to thereby enable replication by DNA as a factor of chromosome or completion of choromosome integration, refers to a phenomenon of artificially causing a genetic change by introducing foreign DNA into a cell.

The method of transformation to be used in the present invention may be any method for transformation, and transformation may be easily performed according to a conventional method in the art. Generally, the transformation method may include a CaCl$_2$ precipitation method; a Hanahan method which increases efficiency using dimethyl sulfoxide (DMSO), which is a reducing material, in the CaCl$_2$ precipitation method; electroporation; a calcium phosphate precipitation method; plasmogamy; a stirring method using silicon carbide fiber; agrobacteria-mediated transformation; transformation using PEG; a dextran sulfate method; lipofectamine and drying/inhibition-mediated transformation, etc.

The method for transformation of the recombinant vector including the nucleic acid encoding the insulin analog according to the present invention is not limited thereto, and any method for transformation or transfection conventionally used in the art may be used without limitation.

The transformant of the present invention may be obtained by introducing the recombinant vector including the nucleic acid encoding the insulin analog into a host cell.

The host suitable for the present invention may not be specifically limited insofar as the host cell enables the expression of the nucleic acid of the present invention. Examples of the host may include *Escherichia* sp. such as *E. coli*; *Bacillus* sp. such as *Bacillus subtilis*; *Pseudomonas* sp. such as *Pseudomonas putida*; yeasts such as *Pichia pastoris*, *Saccharomyces cerevisiae*, and *Schizosaccharomyces pombe*; insec cells such as *Spodoptera frugiperda* (SF9); and animal cells such as CHO, COS, BSC, etc. Preferably, *E. coli* is used as a host cell.

In still another aspect of the present invention, there is provided a formulation capable of increasing the half-life of the insulin analog, increasing the bioavailability, or maintaining sustained activities.

Additionally, the present invention provides long-acting insulin, which is characterized in that a biocompatible material capable of prolonging a half-life is linked to the insulin analog.

Additionally, the present invention provides a conjugate having the Chemical Formula 1 below.

$$X-La-F; \qquad \text{[Chemical Formula 1]}$$

wherein X is an insulin analog having reduced insulin receptor binding affinity compared to the native insulin, L is a linker, a is 0 or a natural number, with the proviso that each L is independent from each other when a is 2 or higher, and F is a material capable of increasing the in-vivo half-life of an insulin analog.

The insulin analog is the same as described above.

According to an exemplary embodiment of the present invention, when the insulin analog is used to increase the half-life and bioavailability of insulin, or applied to a formulation capable of maintaining sustained activities of insulin, the insulin analog can exhibit excellent improvement in half-life and in-vivo activities of insulin, compared to the native insulin.

In particular, in an exemplary embodiment of the present invention, when the material capable of prolonging an in-vivo half-life and the insulin analog are linked together, the resulting insulin analog showed a markedly increased in-vivo half-life.

The formulation capable of increasing the half-life, bioavailability, and maintaining sustained activities of insulin refers to a formulation including a carrier which is directly covalently-bonded to the insulin analog, or a formulation which includes a component capable of increasing the in-vivo activities of the insulin analog.

As used herein, the term "long-acting insulin" refers to a material in which a biocompatible material capable of prolonging a half-life is linked to an insulin analog. The long-acting insulin has the effect of an increased half-life, compared to the native insulin.

As used herein, the term "a biocompatible material or a material capable of increasing a half-life" refers to a material which can be linked to an insulin analog to thereby prolong the half-life of the insulin. As used herein, the term, a biocompatible material capable of prolonging a half-life, can be interchangeably used with the term "carrier".

The biocompatible material or carrier may include any material as long as they can be linked to the insulin analog and prolong the half-life of the insulin, for example, those selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer, but are not limited thereto. The biocompatible material or carrier may be linked to the insulin analog via a covalent or non-covalent bond.

Additionally, the method of linking the insulin analog, which has reduced insulin receptor binding affinity, to the biocompatible material or carrier, which can prolonging the in-vivo half-life, may include a genetic recombination technique, an in-vitro linking, etc., but is not limited to any specific linking method. The FcRn-binding material may be an immunoglobulin Fc region, for example, IgG Fc.

When polyethylene glycol is used as a carrier, the Recode technology by Ambrx, Inc., which enables a position-specific attachment of polyethylene glycol, may be included, and the glycopegylation technology by Neose Technologies, Inc., which enables a specific attachment in the area of glycan, may also be included. Additionally, the method may include a releasable PEG technique, which enables a slow release of polyethylene glycol in the body, but the method is not limited thereto, and methods capable of increasing bioavalability using PEG may also be used. Additionally, a polymer such as polyethylene glycol, polypropylene glycol, copolymers of ethylene glycol-propylene glycol, polyoxytheylated polyol, polyvinyl alcohols, polysaccharides, dextran, polyvinyl ether, biodegradable polymers, lipid polymers, chitins, and hyaluronic acid, may also be linked to the insulin analog, by the above methods.

When albumin is used as a carrier, a technology capable of increasing in-vivo stability by a direct covalent bonding between albumin or an albumin fragment and the insulin analog may be used. Additionally, instead of directly linking albumin to the insulin analog, a technology, which indirectly allows albumin to be linked to the insulin analog by linking a material capable of binding to albumin, e.g., an albumin-specific antibody or antibody fragment thereof, to the insulin analog; and a technology of linking a particular peptide/protein having a binding affinity to albumin (e.g., an albumin-binding peptide produced via Albumod technology by Affibody AB) to the insulin analog, a technology of linking fatty acid or the like having a binding affinity to albumin, etc., may be used, but the method is not limited thereto, and any technology or linking method that can improve in-vivo stability using albumin may be used, without limitation.

In order to increase the in-vivo half-life, a technology using an antibody or antibody fragment thereof as a carrier may be included in the scope of the present invention. It may be an antibody or antibody fragment thereof including an FcRn-bindnig region, or any antibody fragment which does not include the FcRn-binding region such as Fab, etc. The CovX-body technology by CovX Research LLC using a catalytic antibody may be included, and a technology increasing an in-vivo half-life using the immunoglobulin Fc region may also be included in the scope of the present invention.

When the immunoglobulin Fc region is used, the method of linking the Fc region to the insulin analog and a linker thereof may be a peptide bond and polyethylene glycol and the like, but is not limited thereto, and any chemical linking method may be used. Additionally, the linking ratio between the Fc region and the insulin analog may be 1:1 or 1:2, but is not limited thereto.

The immunoglobulin Fc region is safe for use as a drug carrier because it is a biodegradable polypeptide metabolized in-vivo. Also, the immunoglobulin Fc region has a relatively low molecular weight, as compared to the whole immunoglobulin molecules, and thus, it is advantageous in terms of preparation, purification, and yield of the conjugate. The immunoglobulin Fc region does not contain a Fab fragment, which is highly non-homogenous due to different amino acid sequences according to the antibody subclasses, and thus it can be expected that the immunoglobulin Fc region may markedly increase the homogeneity of substances and be less antigenic in blood.

As used herein, the term "immunoglobulin Fc region" refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains of the immunoglobulin, as long as it has an effect substantially similar to or better than that of the native form. Also, it may be a fragment having a deletion in a relatively long portion of the amino acid sequence of CH2 and/or CH3.

That is, the immunoglobulin Fc region of the present invention may include 1) a CH1 domain, a CH2 domain, a CH3 domain, and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

Further, the immunoglobulin Fc region of the present invention includes a sequence variant (mutant) thereof as well as a native amino acid sequence. An amino acid sequence derivative has a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification.

Additionally, other various kinds of variants are possible, including variants having a deletion of a region capable of forming a disulfide bond, a deletion of several amino acid residues at the N-terminus of a native Fc form, or an addition of methionine residue to the N-terminus of a native Fc form. Furthermore, in order to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions.

The Fc region, if desired, may be modified by phosphorylation, sulfation, acrylation, glycosylation, methylation, farnesylation, acetylation, amidation, or the like.

The aforementioned Fc derivatives are derivatives that have a biological activity identical to that of the Fc region of the present invention or improved structural stability against heat, pH, or the like.

In addition, these Fc regions may be obtained from native forms isolated from humans and other animals including cows, goats, swine, mice, rabbits, hamsters, rats, and guinea pigs, or may be recombinants or derivatives thereof, obtained from transformed animal cells or microorganisms. Here, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)$_2$. These fragments may be subjected to size-exclusion chromatography to isolate Fc or pF'c.

Preferably, a human-derived Fc region is a recombinant immunoglobulin Fc region that is obtained from a microorganism.

In addition, the immunoglobulin Fc region may be in the form of having native sugar chains, increased sugar chains compared to a native form or decreased sugar chains compared to the native form, or may be in a deglycosylated form. The increase, decrease, or removal of the immunoglobulin Fc sugar chains may be achieved by methods common in the art, such as a chemical method, an enzymatic method and a genetic engineering method using a microorganism. Here, the removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

The term "deglycosylation", as used herein, means to enzymatically remove sugar moieties from an Fc region, and the term "aglycosylation" means that an Fc region is produced in an unglycosylated form by a procaryote, preferably, E. coli.

On the other hand, the immunoglobulin Fc region may be derived from humans or other animals including cows, goats, swine, mice, rabbits, hamsters, rats, and guinea pigs, and preferably humans. In addition, the immunoglobulin Fc region may be an Fc region that is derived from IgG, IgA, IgD, IgE, and IgM, or that is made by combinations thereof or hybrids thereof. Preferably, it is derived from IgG or IgM, which is among the most abundant proteins in human blood, and most preferably, from IgG which is known to enhance the half-lives of ligand-binding proteins.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1 CH2, CH3, and CH4 of IgG Fc, IgM Fc, IgA Fc, IgE Fc, and IgD Fc, and may include the hinge region.

On the other hand, IgG is divided into IgG1, IgG2, IgG3, and IgG4 subclasses, and the present invention includes combinations and hybrids thereof. Preferred are IgG2 and IgG4 subclasses, and most preferred is the Fc region of IgG4 rarely having effector functions such as complement dependent cytotoxicity (CDC). That is, as the drug carrier of the present invention, the most preferable immunoglobulin Fc region is a human IgG4-derived non-glycosylated Fc region. The human-derived Fc region is more preferable than a non-human derived Fc region which may act as an antigen in the human body and cause undesirable immune responses such as the production of a new antibody against the antigen.

In order to increase the in-vivo half-life, a technology of linking a peptide or a protein fragment to the insulin analog may also be included in the scope of the present invention. The peptide or protein fragment to be used may be an elastin-like polypeptide (ELP) of repeating units of a particular amino acid sequence, and the Xten technology using an artificial polypeptide by Versartis, Inc. is also included in the scope of the present invention. Additionally, the structure inducing probe (SIP) technology of increasing the in-vivo half-life using the multi-lysine by Zealandd, CTP fusion technology by Prolor Biotech Inc. are also included, and transferrin, which is known to have high in-vivo stability, or fibronectin, which is a constituting component of connective tissues, and derivatives thereof, etc., may also be included. The peptides or proteins to be linked to the insulin analog are not limited to the above, but any peptide or protein that can increase the in-vivo half-life of the insulin analog may be included in the scope of the present invention.

Additionally, the carrier to be used for increasing the in-vivo half-life may be a non-peptide material such as a polysaccharide or a fatty acid, etc.

The insulin analog, which has reduced insulin receptor binding affinity compared to the native insulin, and the carrier, which can increase the in-vivo half-life of the insulin analog, may be linked via a linker.

The linker may be a peptide linker or a non-peptide linker, and for example, may be one selected from the group consisting of polyethylene glycol, fatty acid, saccharide, a polymer, a low molecular weight compound, a nucleotide, and a combination thereof.

The polymer may be a non-peptide linker selected from the group consisting of polypropylene glycol, copolymers of ethylene glycol-propylene glycol, polyoxytheylated polyol, polyvinyl alcohols, polysaccharides, dextran, polyvinyl ether, biodegradable polymers, lipid polymers, chitins, hyaluronic acid, oligonucleotides, and a combination thereof, but is not limited thereto. The biodegradable polymer may include biodegradable polymers such as polylactic acid (PLA) and polylactic-glycolic acid (PLGA).

The non-peptide linker of the present invention may include not only those described above but also the derivatives thereof well known in the art and those which can be easily prepared within the skill of the art are also included in the scope of the present invention.

The linking by the linker may be any chemical bond such as a covalent chemical bond or a non-covalent chemical bond, without limitation.

More specifically, in the present invention, the non-peptide polymer means a biocompatible polymer including two or more repeating units linked to each other, in which the repeating units are linked by any covalent bond excluding the peptide bond. Such non-peptide polymer may have two ends or three ends.

The peptide linker which is used in the fusion protein obtained by a conventional inframe fusion method has drawbacks in that it is easily cleaved in the body by a proteolytic enzyme, and thus a sufficient effect of increasing the blood half-life of the active drug by a carrier may not be obtained as expected. In the present invention, however, the conjugate may be prepared using the non-peptide linker as well as the peptide linker. In the non-peptide linker, the polymer having resistance to the proteolytic enzyme may be used to maintain the blood half-life of the peptide being similar to that of the carrier. Therefore, any non-peptide polymer can be used without limitation, as long as it is a polymer having the aforementioned function, that is, a polymer having resistance to the in-vivo proteolytic enzyme. The non-peptide polymer has a molecular weight ranging from 1 kDa to 100 kDa, and preferably, from 1 kDa to 20 kDa.

Additionally, the non-peptide polymer of the present invention, linked to the immunoglobulin Fc region, may be one kind of polymer or a combination of different kinds of polymers.

The non-peptide polymer used in the present invention has a reactive group capable of binding to the immunoglobulin Fc region and the protein drug.

The non-peptide polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptide polymer has a reactive aldehyde group at both ends thereof, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to a N-terminus at a low pH, and binds to a lysine residue to form a covalent bond at a high pH, such as pH 9.0.

The reactive groups at both ends of the non-peptide polymer may be the same as or different from each other. For example, the non-peptide polymer may possess a maleimide group at one end, and an aldehyde group, a propionaldehyde group, or a butyraldehyde group at the other end. When a polyethylene glycol having a reactive hydroxy group at both ends thereof is used as the non-peptide polymer, the hydroxy group may be activated to various reactive groups by known chemical reactions, or a polyethylene glycol having a commercially available modified reactive group may be used so as to prepare the single chain insulin analog conjugate of the present invention.

Additionally, when the insulin analog and the biocompatible material are linked to each other by a linker, each end of the non-peptide linker may be linked to an amine group or thiol group of the biocompatible material and the insulin analog, respectively.

In a more exemplary embodiment, the insulin analog and the biocompatible material may be linked by a linker interposed therebetween, and the biocompatible material may be an FcRn-binding material, wherein the linker is a peptide linker or a non-peptide linker selected from the group consisting of polyethylene glycol, polypropylene glycol, copolymers of ethylene glycol-propylene glycol, polyoxytheylated polyol, polyvinyl alcohols, polysaccharides, dextran, polyvinyl ether, biodegradable polymers, lipid polymers, chitins, hyaluronic acid, and a combination thereof.

Meanwhile, the formulations that can increase bioavailability or maintain sustained activities may include sustained release formulations by microparticles and nanoparticles using PLGA, hyaluronic acid, chitosan, etc.

Additionally, examples of other forms of formulations that can increase bioavailability or maintain sustained activities may include implants, inhalations, and nasal formulations, and patches.

The insulin analog conjugate of the present invention can maintain in-vivo activities of the conventional insulin such as energy metabolism and sugar metabolism, and also increase the blood half-life of the insulin analog and markedly increase duration of in-vivo efficacy of the peptide, and therefore, the conjugate is useful in the treatment of diabetes.

In another exemplary embodiment of the present invention, there is provided a method for preparing long-acting insulin, including (a) preparing (i) an insulin analog; and (ii) a biocompatible material selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer, respectively; and (b) linking the insulin analog to the biocompatible material.

The insulin analog, the biocompatible material, and the long-acting insulin are the same as described above.

In another aspect, the present invention provides a long-acting insulin formulation including the insulin analog conjugate. The long-acting insulin formulation may be a long-acting insulin formulation having increased in-vivo duration and stability. The long-acting formulation may be a pharmaceutical composition for the treatment of diabetes, but is not limited thereto.

The pharmaceutical composition including the conjugate of the present invention may include pharmaceutically acceptable carriers. For oral administration, the pharmaceutically acceptable carrier may include a binder, a lubricant, a disintegrator, an excipient, a solubilizer, a dispersing agent, a stabilizer, a suspending agent, a coloring agent, a perfume, or the like. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, a preserving agent, etc. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups, or wafers. For injectable preparations, the pharmaceutical composition may be formulated into a single-dose ampule or a multidose container. The pharmaceutical composition may also be formulated into solutions, suspensions, tablets, pills, capsules, and sustained-release preparations.

On the other hand, examples of carriers, excipients, and diluents suitable for formulation include lactose, dextrose, sucrose, sorbitol, mannitol, xylitol, erythritol, maltitol, starch, acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oils, etc.

In addition, the pharmaceutical formulations may further include fillers, anti-coagulating agents, lubricants, humectants, perfumes, antiseptics, etc.

In still another aspect, the present invention provides a method for treating insulin-related diseases, including administering the insulin analog or the insulin analog conjugate to a subject in need thereof.

The conjugate according to the present invention is useful in the treatment of diabetes, and therefore, the disease can be treated by administering the pharmaceutical composition including the same.

The term "administration", as used herein, refers to introduction of a predetermined substance into a patient by a certain suitable method. The conjugate of the present invention may be administered via any of the common routes, as long as it is able to reach a desired tissue. Intraperitoneal, intravenous, intramuscular, subcutaneous, intradermal, oral, topical, intranasal, intrapulmonary, and intrarectal administration may be performed, but the present invention is not limited thereto. However, since peptides are digested upon oral administration, active ingredients of a composition for oral administration should be coated or formulated for protection against degradation in the stomach. Preferably, the present composition may be administered in an injectable form. In addition, the pharmaceutical composition may be administered using a certain apparatus capable of transporting the active ingredients into a target cell.

Further, the pharmaceutical composition of the present invention may be determined by several related factors including the types of diseases to be treated, administration routes, the patient's age, gender, and weight, and severity of the illness, as well as by the types of the drug as an active component. Since the pharmaceutical composition of the present invention has excellent in-vivo duration and titer, it has an advantage of greatly reducing administration frequency of the pharmaceutical formulation of the present invention.

BEST MODE

Hereinafter, the present invention will be described in more detail with reference to Examples. However, these Examples are for illustrative purposes only, and the invention is not intended to be limited by these Examples.

Example 1: Preparation of Single Chain Insulin Analog-Expressing Vector

In order to prepare insulin analogs, each of them having a modified amino acid in the A chain or the B chain, using the native insulin-expressing vector as a template, forward and reverse oligonucleotides were synthesized (Table 2), and then PCR was carried out to amplify each analog gene.

In the following Table 1, amino acid sequences modified in the A chain or the B chain and analog names are given. That is, Analog 1 represents that the 1$^{st}$ glycine of the A chain is substituted with alanine, and Analog 4 represents that the 8$^{th}$ glycine of the B chain is substituted with alanine.

TABLE 1

| Analogs | Modified sequence |
| --- | --- |
| Analog 1 | A$^1$G->A |
| Analog 2 | A$^2$I->A |

TABLE 1-continued

| Analogs | Modified sequence |
| --- | --- |
| Analog 3 | A$^{19}$Y->A |
| Analog 4 | B$^8$G->A |
| Analog 5 | B$^{23}$G->A |
| Analog 6 | B$^{24}$F->A |
| Analog 7 | B$^{25}$F->A |
| Analog 8 | A$^{14}$Y->E |
| Analog 9 | A$^{14}$Y->N |

Primers for insulin analog amplification are given in the following Table 2.

TABLE 2

| Analogs | Sequence | SEQ ID NO. |
| --- | --- | --- |
| Analog 1 | 5' GGGTCCCTGCAGAAGCGTGCGATTGTGGAACAATGCTGT 3' | SEQ ID NO. 1 |
| | 5' ACAGCATTGTTCCACAATCGCACGCTTCTGCAGGGACCC 3' | SEQ ID NO. 2 |
| Analog 2 | 5' TCCCTGCAGAAGCGTGGCGCGGTGGAACAATGCTGTACC 3' | SEQ ID NO. 3 |
| | 5' GGTACAGCATTGTTCCACCGCGCCACGCTTCTGCAGGGA 3' | SEQ ID NO. 4 |
| Analog 3 | 5' CTCTACCAGCTGGAAAACGCGTGTAACTGAGGATCC 3' | SEQ ID NO. 5 |
| | 5' GGATCCTCAGTTACACGCGTTTTCCAGCTGGTAGAG 3' | SEQ ID NO. 6 |
| Analog 4 | 5' GTTAACCAACACTTGTGTGCGTCACACCTGGTGGAAGCT 3' | SEQ ID NO. 7 |
| | 5' AGCTTCCACCAGGTGTGACGCACACAAGTGTTGGTTAAC 3' | SEQ ID NO. 8 |
| Analog 5 | 5' CTAGTGTGCGGGGAACGAGCGTTCTTCTACACACCCAAG 3' | SEQ ID NO. 9 |
| | 5' CTTGGGTGTGTAGAAGAACGCTCGTTCCCCGCACACTAG 3' | SEQ ID NO. 10 |
| Analog 6 | 5' GTGTGCGGGGAACGAGGCGCGTTCTACACACCCAAGACC 3' | SEQ ID NO. 11 |
| | 5' GGTCTTGGGTGTGTAGAACGCGCCTCGTTCCCCGCACAC 3' | SEQ ID NO. 12 |
| Analog 7 | 5' TGCGGGGAACGAGGCTTCGCGTACACACCCAAGACCCGC 3' | SEQ ID NO. 13 |
| | 5' GCGGGTCTTGGGTGTGTACGCGAAGCCTCGTTCCCCGCA 3' | SEQ ID NO. 14 |
| Analog 8 | 5'-CCAGCATCTGCTCCCTCGAACAGCTGGAGAACTACTG-3' | SEQ ID NO. 15 |
| | 5'-Cagtagttctccagctgttcgagggagcagatgctgg-3' | SEQ ID NO. 16 |
| Analog 9 | 5'-CAGCATCTGCTCCCTCAACCAGCTGGAGAACTAC-3' | SEQ ID NO. 17 |
| | 5'-Gtagttctccagctggttgagggagcagatgctg-3' | SEQ ID NO. 18 |

A PCR reaction for insulin analog amplification was carried out under conditions of 95° C. for 30 seconds, 55° C. for 30 seconds, and 68° C. for 6 minutes, for 18 cycles. The insulin analog fragments obtained under the conditions were inserted into pET22b vector to be expressed as intracellular inclusion bodies, and the resulting expression vectors were designated as pET22b-insulin analogs 1 to 9. The expression vectors contained nucleic acids encoding amino acid sequences of insulin analogs 1 to 9 under the control of T7 promoter, and insulin analog proteins were expressed as inclusion bodies in host cells.

DNA sequences and protein sequences of insulin analogs 1 to 9 are given in the following Table 3.

TABLE 3

| Analog | | SEQ ID NO: |
| --- | --- | --- |
| Analog 1 DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GCG ATT GTG GAA CAA TGC TGT ACC AGC ATC TGC TCC CTC TAC CAG CTG GAG AAC TAC TGC AAC | 19 |

TABLE 3-continued

| Analog | | | SEQ ID NO: |
|---|---|---|---|
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Ala Ile Val Glu Gln Cys Cys Thr Ser Ile Cys Ser Leu Tyr Gln Leu Glu Asn Tyr Cys Asn | 20 |
| Analog 2 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 21 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ala Val Glu Gln Cys Cys Thr Ser Ile Cys Ser Leu Tyr Gln Leu Glu Asn Tyr Cys Asn | 22 |
| Analog 3 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC GCG TGC AAC | 23 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Ala Cys Asn | 24 |
| Analog 4 | DNA | TTC GTT AAC CAA CAC TTG TGT GCG TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 25 |
| | Protein | Phe Val Asn Gln His Leu Cys Ala Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 26 |
| Analog 5 | DNA | TTC GTT AAC CAA CAC TTG TGT GGC TCA CAC CTG GTG GAA GCT CTC TAC CTA GTG TGC GGG GAA CGA GCG TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 27 |
| | Protein | Phe Val Asn Gln His Leu Cys Gly Ser His Leu Val Glu Ala Leu Tyr Leu Val Cys Gly Glu Arg Ala Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 28 |

TABLE 3-continued

| Analog | | | SEQ ID NO: |
|---|---|---|---|
| Analog 6 | DNA | TTC GTT AAC CAA CAC TTG TGT GGC TCA CAC CTG GTG GAA GCT CTC TAC CTA GTG TGC GGG GAA CGA GGC GCG TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 29 |
| | Protein | Phe Val Asn Gln His Leu Cys Gly Ser His Leu Val Glu Ala Leu Tyr Leu Val Cys Gly Glu Arg Gly Ala Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 30 |
| Analog 7 | DNA | TTC GTT AAC CAA CAC TTG TGT GGC TCA CAC CTG GTG GAA GCT CTC TAC CTA GTG TGC GGG GAA CGA GGC TTC GCG TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 31 |
| | Protein | Phe Val Asn Gln His Leu Cys Gly Ser His Leu Gly Phe Ala Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 32 |
| Analog 8 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC GAA CAG CTG GAG AAC TAC TGC AAC TGA | 33 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Glu Gln Leu Glu Asn Tyr Cys Asn | 34 |
| Analog 9 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC AAC CAG CTG GAG AAC TAC TGC AAC TGA | 35 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Asn Gln Leu Glu Asn Tyr Cys Asn | 36 |

Example 2: Expression of Recombinant Insulin Analog Fusion Peptide

Expressions of recombinant insulin analogs were carried out under the control of T7 promoter. *E. coli* BL21-DE3 (*E. coli* B F-dcm ompT hsdS(rB-mB-) gal λDE3; Novagen) was transformed with each of the recombinant insulin analog-expressing vectors. Transformation was performed in accordance with the recommended protocol (Novagen). Single colonies transformed with each recombinant expression vector were collected and inoculated in 2× Luria Broth (LB) containing ampicillin (50 µg/mL) and cultured at 37° C. for 15 hours. The recombinant strain culture broth and 2×LB medium containing 30% glycerol were mixed at a ratio of 1:1 (v/v). Each 1 mL was dispensed to a cryotube and stored at −140° C., which was used as a cell stock for production of the recombinant fusion protein.

To express the recombinant insulin analogs, 1 vial of each cell stock was thawed and inoculated in 500 mL of 2× Luria broth, and cultured with shaking at 37° C. for 14 hours to 16 hours. The cultivation was terminated, when OD600 reached 5.0 or higher. The culture broth was used as a seed culture broth. This seed culture broth was inoculated to a 50 L fermentor (MSJ-U2, B.E.MARUBISHI, Japan) containing 17 L of fermentation medium, and initial bath fermentation was started. The culture conditions were maintained at a temperature of 37° C., an air flow rate of 20 L/min (1 vvm), an agitation speed of 500 rpm, and at pH 6.70 using a 30% ammonia solution. Fermentation was carried out in fed-batch mode by adding a feeding solution, when nutrients were depleted in the culture broth. Growth of the strain was monitored by OD value. IPTG was introduced in a final concentration of 500 µM, when OD value was above 100. After introduction, the cultivation was further carried out for about 23 hours to 25 hours. Upon termination of the cultivation, the recombinant strains were harvested by centrifugation and stored at −80° C. until use.

Example 3: Recovery and Refolding of Recombinant Insulin Analogs

In order to change the recombinant insulin analogs expressed in Example 2 into soluble forms, cells were disrupted, followed by refolding. 100 g (wet weight) of the cell pellet was resuspended in 1 L lysis buffer (50 mM Tris-HCl (pH 9.0), 1 mM EDTA (pH 8.0), 0.2 M NaCl and 0.5% Triton X-100). The cells were disrupted using a microfluidizer processor M-110EH (AC Technology Corp. Model M1475C) at an operating pressure of 15,000 psi. The thus-disrupted cell lysate was centrifuged at 7,000 rpm and 4° C. for 20 minutes. The supernatant was discarded and the pellet was resuspended in 3 L washing buffer (0.5% Triton X-100 and 50 mM Tris-HCl (pH 8.0), 0.2 M NaCl, 1 mM EDTA). After centrifugation at 7,000 rpm and 4° C. for 20 minutes, the cell pellet was resuspended in distilled water, followed by centrifugation in the same manner. The thus-obtained pellet was resuspended in 400 mL of buffer (1 M Glycine, 3.78 g Cysteine-HCl, pH 10.6) and stirred at room temperature for 1 hour. To recover the recombinant insulin analog thus re-suspended, 400 mL of 8 M urea was added and stirred at 40° C. for 1 hour. For refolding of the solubilized recombinant insulin analogs, centrifugation was carried out at 7,000 rpm and 4° C. for 30 minutes, and the supernatant was collected. 7.2 L of distilled water was added thereto using a peristaltic pump at a flow rate of 1000 mL/hr while stirring at 4° C. for 16 hours.

Example 4: Cation Binding Chromatography Purification

The refolded sample was loaded onto a Source S (GE healthcare) column equilibrated with 20 mM sodium citrate (pH 2.0) buffer containing 45% ethanol, and then the insulin analog proteins were eluted in 10 column volumes with a linear gradient from 0% to 100% 20 mM sodium citrate (pH 2.0) buffer containing 0.5 M potassium chloride and 45% ethanol.

Example 5: Trypsin and Carboxypeptidase B Treatment

Salts were removed from the eluted samples using a desalting column, and the buffer was exchanged with a buffer (10 mM Tris-HCl, pH 8.0). With respect to the obtained sample protein, trypsin corresponding to 1000 molar ratio and carboxypeptidase B corresponding to 2000 molar ratio were added, and then stirred at 16° C. for 16 hours. To terminate the reaction, 1 M sodium citrate (pH 2.0) was used to reduce pH to 3.5.

Example 6: Cation Binding Chromatography Purification

The thus-reacted sample was loaded onto a Source S (GE healthcare) column equilibrated with 20 mM sodium citrate (pH 2.0) buffer containing 45% ethanol, and then the insulin analog proteins were eluted in 10 column volumes with a linear gradient from 0% to 100% 20 mM sodium citrate (pH 2.0) buffer containing 0.5 M potassium chloride and 45% ethanol.

Example 7: Anion Binding Chromatography Purification

Salts were removed from the eluted sample using a desalting column, and the buffer was exchanged with a buffer (10 mM Tris-HCl, pH 7.5). In order to isolate a pure insulin analog from the sample obtained in Example 6, the sample was loaded onto an anion exchange column (Source Q: GE healthcare) equilibrated with 10 mM Tris (pH 7.5) buffer, and the insulin analog protein was eluted in 10 column volumes with a linear gradient from 0% to 100% 10 mM Tris (pH 7.5) buffer containing 0.5 M sodium chloride.

The purity of the thus-purified insulin analog was analyzed by protein electrophoresis (SDS-PAGE, FIG. 1) and high pressure chromatography (HPLC) (FIG. 2), and modifications of amino acids were identified by peptide mapping (FIG. 3) and molecular weight analysis of each peak.

As a result, each insulin analog was found to have the desired modification in its amino acid sequence.

Example 8: Preparation of Insulin Analog (No. 7)-Immunoglobulin Fc Conjugate To pegylate the N-terminus of the beta chain of the insulin analog using 3.4K ALD2 PEG (NOF, Japan), the insulin analog and PEG were reacted at a molar ratio of 1:4 with an insulin analog concentration of 5 mg/mL at 4° C. for about 2 hours. At this time, the reaction was performed in 50 mM sodium citrate at pH 6.0 and 45% isopropanol. 3.0 mM sodium cyanoborohydride was added as a reducing agent and was allowed to react. The reaction solution was purified with SP-HP (GE Healthcare, USA) column using a buffer containing sodium citrate (pH 3.0) and 45% ethanol, and KCl concentration gradient.

To prepare an insulin analog-immunoglobulin Fc fragment conjugate, the purified mono-PEGylated insulin analog and the immunoglobulin Fc fragment were reacted at a molar ratio of 1:1 to 1:2 and at 25° C. for 13 hours, with a total protein concentration of about 20 mg/mL. At this time, the reaction buffer conditions were 100 mM HEPES at pH 8.2, and 20 mM sodium cyanoborohydride as a reducing agent was added thereto. Therefore, PEG was bound to the N-terminus of the Fc fragment.

After the reaction was terminated, the reaction solution was loaded onto the Q HP (GE Healthcare, USA) column with Tris-HCl (pH 7.5) buffer and NaCl concentration gradient to separate and purify unreacted immunoglobulin Fc fragment and mono-PEGylated insulin analog.

Thereafter, Source 15ISO (GE Healthcare, USA) was used as a secondary column to remove the remaining immunoglobulin Fc fragment and the conjugate, in which two or more insulin analogs were linked to the immunoglobulin Fc fragment, thereby obtaining the insulin analog-immunoglobulin Fc fragment conjugate. At this time, elution was carried out using a concentration gradient of ammonium sulfate containing Tris-HCl (pH 7.5), and the insulin analog-immunoglobulin Fc conjugate thus eluted was analyzed by protein electrophoresis (SDS-PAGE, FIG. 4) and high pressure chromatography (HPLC) (FIG. 5).

As a result, the conjugate was found to have almost 99% purity.

Example 9: Comparison of Insulin Receptor Binding Affinity Between Native Insulin, Insulin Analog, Native Insulin-Immunoglobulin Fc Conjugate, and Insulin Analog-Immunoglobulin Fc Conjugate In order to measure the insulin receptor binding affinity of the insulin analog-immunoglobulin Fc conjugate, Surface plasmon resonance (SPR, BIACORE 3000, GE healthcare) was used for analysis. Insulin receptors were immobilized on a CM5 chip by amine coupling, and 5 dilutions or more of native insulin, insulin analog, native insulin-immunoglobulin Fc conjugate, and insulin analog-immunoglobulin Fc conjugate were applied thereto, independently. Then, the insulin receptor binding affinity of each substance was examined. The binding affinity of each substance was calculated using BIAevaluation software. At this time, the model used was 1:1 Langmuir binding with baseline drift.

As a result, compared to human insulin, insulin analog (No. 6) showed receptor binding affinity of 14.8%, insulin analog (No. 7) showed receptor binding affinity of 9.9%, insulin analog (No. 8) showed receptor binding affinity of 57.1%, insulin analog (No. 9) showed receptor binding affinity of 78.8%, native insulin-immunoglobulin Fc conjugate showed receptor binding affinity of 3.7% to 5.9% depending on experimental runs, insulin analog (No. 6)-immunoglobulin Fc conjugate showed receptor binding affinity of 0.9% or less, insulin analog (No. 7)-immunoglobulin Fc conjugate showed receptor binding affinity of 1.9%, insulin analog (No. 8)-immunoglobulin Fc conjugate showed receptor binding affinity of 1.8%, and insulin analog (No. 9)-immunoglobulin Fc conjugate showed receptor binding affinity of 3.3% (Table 4). As such, it was observed that the insulin analogs of the present invention had reduced insulin receptor binding affinity, compared to the native insulin, and the insulin analog-immunoglobulin Fc conjugates also had remarkably reduced insulin receptor binding affinity.

TABLE 4

Comparison of insulin receptor binding affinity

| Test No. | Substance name | $k_a$ (1/Ms, ×10$^5$) | $k_d$ (1/s, ×10$^{-3}$) | $K_D$ (nM) |
|---|---|---|---|---|
| Test 1 | Native human insulin | 2.21 (100%) | 7.47 (100%) | 35.05 (100%) |
| | Insulin analog (No. 6) | 0.28 (12.6%) | 6.60 (88.4%) | 237.0 (14.8%) |
| Test 2 | Native human insulin | 2.29 (100%) | 10.1 (100%) | 46.1 (100%) |
| | Native insulin-immunoglobulin Fc conjugate | 0.09 (3.9%) | 7.8 (77.2%) | 781.3 (5.9%) |
| | Insulin analog (No. 6)-immunoglobulin Fc conjugate | 0.02 (0.9%) | 10.1 (100%) | 5260.0 (0.9%) |
| Test 3 | Native human insulin | 1.76 (100%) | 10.73 (100%) | 63.47 (100%) |
| | Insulin analog (No. 7) | 0.14 (7.8%) | 8.34 (77.7%) | 642.0 (9.9%) |
| | Native insulin-immunoglobulin Fc conjugate | 0.05 (2.7%) | 5.85 (54.5%) | 1236.67 (5.1%) |
| | Insulin analog (No. 7)-immunoglobulin Fc conjugate | 0.02 (1.3%) | 7.20 (67.1%) | 3270.0 (1.9%) |
| Test 4 | Native human insulin | 2.9 (100%) | 12.4 (100%) | 42.0 (100%) |
| | Insulin analog (No. 8) | 1.78 (60.0%) | 12.9 (104.6%) | 73.4 (57.1%) |
| | Native insulin-immunoglobulin Fc conjugate | 0.06 (2.1%) | 6.9 (56.1%) | 1140.0 (3.7%) |
| | Insulin analog (No. 8)-immunoglobulin Fc conjugate | 0.03 (0.9%) | 6.4 (51.6%) | 2320.0 (1.8%) |
| Test 5 | Native human insulin | 2.0 (100%) | 9.7 (100%) | 50.4 (100%) |
| | Insulin analog (No. 9) | 1.85 (92.5%) | 11.9 (122.5%) | 64.0 (78.8%) |
| | Native insulin-immunoglobulin Fc conjugate | 0.09 (4.3%) | 7.4 (76.5%) | 862.0 (5.9%) |
| | Insulin analog (No. 9)-immunoglobulin Fc conjugate | 0.05 (2.4%) | 7.3 (75.0%) | 1536.7 (3.3%) |

Example 10: Comparison of In-Vitro Efficacy Between Native Insulin-Immunoglobulin Fc Conjugate and Insulin Analog-Immunoglobulin Fc Conjugate In order to evaluate in-vitro efficacy of the insulin analog-immunoglobulin Fc conjugate, mouse-derived differentiated 3T3-L1 adipocytes were used to test glucose uptake or lipid synthesis. 3T3-L1 cells were subcultured in 10% NBCS (newborn calf serum)-containing DMEM (Dulbeco's Modified Eagle's Medium, Gibco, Cat. No, 12430) twice or three times a week, and maintained. 3T3-L1 cells were suspended in a differentiation medium (10% FBS-containing DMEM), and then inoculated at a density of 5×10$^4$ per well in a 48-well dish, and cultured for 48 hours. For adipocyte differentiation, 1 µg/mL human insulin (Sigma, Cat. No. 19278), 0.5 mM IBMX (3-isobutyl-1-methylxanthine, Sigma, Cat. No. I5879), and 1 µM Dexamethasone (Sigma, Cat. No. D4902) were mixed with the differentiation medium, and 250 µL of the mixture was added to each well, after removing the previous medium. After 48 hours, the medium was replaced with the differentiation medium supplemented with only 1 μg/mL of human insulin. Thereafter, while the medium was exchanged with the differentiation medium supplemented with 1 μg/mL of human insulin every 48 hours, induction of adipocyte differentiation was examined for 7 days to 9 days. To test glucose uptake, the differentiated cells were washed with serum-free DMEM medium once, and then 250 μL was added to induce serum depletion for 4 hours. Serum-free DMEM medium was used to carry out 10-fold serial dilutions for Human insulin from 10 μM to 0.01 μM, and for native insulin-immunoglobulin Fc conjugate and insulin analog-immunoglobulin Fc conjugates from 20 μM to 0.02 μM. Each 250 μL of the thus-prepared samples was added to cells, and cultured in a 5% $CO_2$ incubator at 37° C. for 24 hours. In order to measure the residual amount of glucose in the medium after incubation, 200 μL of the medium was taken and diluted 5-fold with D-PBS, followed by GOPOD assay (GOPOD Assay Kit, Megazyme, Cat. No. K-GLUC). Based on the absorbance of glucose standard solution, the concentration of glucose remaining in the medium was converted, and EC50 values for glucose uptake of native insulin-immunoglobulin Fc conjugate and insulin analog-immunoglobulin Fc conjugates were calculated, respectively.

As a result, compared to human insulin, native insulin-immunoglobulin Fc conjugate showed glucose uptake of 11.6%, insulin analog (No. 6)-immunoglobulin Fc conjugate showed glucose uptake of 0.43%, insulin analog (No. 7)-immunoglobulin Fc conjugate showed glucose uptake of 1.84%, insulin analog (No. 8)-immunoglobulin Fc conjugate showed glucose uptake of 16.0%, insulin analog (No. 9)-immunoglobulin Fc conjugate showed glucose uptake of 15.1% (Table 5).

As such, it was observed that the insulin analog (No. 6)-immunoglobulin Fc conjugate and insulin analog (No. 7)-immunoglobulin Fc conjugate of the present invention had remarkably reduced in-vitro titer, compared to native insulin-immunoglobulin Fc conjugate, and insulin analog (No. 8)-immunoglobulin Fc conjugate and insulin analog (No. 9)-immunoglobulin Fc conjugate had in-vitro titer similar to that of the native insulin-immunoglobulin Fc conjugate.

TABLE 5

| Test No. | Substance name | Glucose uptake (relative to native insulin) |
| --- | --- | --- |
| Test 1 | Native human insulin | 100% |
|  | Native insulin-immunoglobulin Fc conjugate | 11.6% |
|  | Insulin Analog No. 6-immunoglobulin Fc conjugate | 0.43% |
|  | Insulin Analog No. 7-immunoglobulin Fc conjugate | 1.84% |
| Test 2 | Native human insulin | 100% |
|  | Native insulin-immunoglobulin Fc conjugate | 15.2% |
|  | Insulin Analog No. 8-immunoglobulin Fc conjugate | 16.0% |
| Test 3 | Native human insulin | 100% |
|  | Native insulin-immunoglobulin Fc conjugate | 11.7% |
|  | Insulin Analog No. 9-immunoglobulin Fc conjugate | 15.1% |

Example 11: Pharmacokinetics of Insulin Analog-Immunoglobulin Fc Conjugate

In order to examine pharmacokinetics of the insulin analog-immunoglobulin Fc conjugates, their blood concentration over time was compared in normal rats (6-week old, male SD rat) adapted for 5 days to the laboratory. 21.7 nmol/kg of native insulin-immunoglobulin Fc conjugate and 65.1 nmol/kg of insulin analog-immunoglobulin Fc conjugate were subcutaneously injected, respectively. The blood was collected at 0, 1, 4, 8, 24, 48, 72, 96, 120, 144, 168, 192, and 216 hours. At each time point, blood concentrations of native insulin-immunoglobulin Fc conjugate and insulin analog-immunoglobulin Fc conjugate were measured by enzyme linked immunosorbent assay (ELISA), and Insulin ELISA (ALPCO, USA) was used as a kit. However, as a detection antibody, mouse anti-human IgG4 HRP conjugate (Alpha Diagnostic Intl, Inc, USA) was used.

The results of examining pharmacokinetics of the native insulin-immunoglobulin Fc conjugate and the insulin analog-immunoglobulin Fc conjugate showed that their blood concentrations increased in proportion to their administration concentrations, and the insulin analog-immunoglobulin Fc conjugates having low insulin receptor binding affinity showed a highly increased half-life, compared to the native insulin-Fc conjugate (FIG. 6).

These results suggest that when the insulin analogs of the present invention modified to have reduced insulin receptor binding affinity are linked to immunoglobulin Fc region to prepare conjugates, the conjugates can be provided as stable insulin formulations due to a remarkably increased in-vivo blood half-life, and thus effectively used as therapeutic agents for diabetes.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A long-acting insulin, wherein a biocompatible material capable of prolonging a half-life is linked to an insulin analog, said insulin analog having a reduced insulin receptor binding affinity compared to a native insulin, and
said insulin analog including the A chain of SEQ ID NO: 37 of the following Formula 1 and the B chain of SEQ ID NO: 38 of the following Formula 2:

Formula 1:

[Formula 1]
(SEQ ID NO: 37)
Xaa1-Xaa2-Val-Glu-Gln-Cys-Cys-Thr-Ser-Ile-Cys-Ser-

Leu-Xaa3-Gln-Leu-Glu-Asn-Xaa4-Cys-Asn wherein
Xaa1 is glycine,
Xaa2 is isoleucine or alanine,
Xaa3 is tyrosine, glutamic acid, or asparagine, and
Xaa4 is tyrosine or alanine; and
Formula 2:

[Formula 2]
(SEQ ID NO: 38)
Phe-Val-Asn-Gln-His-Leu-Cys-Xaa5-Ser-His-Leu-Val-

Glu-Ala-Leu-Tyr-Leu-Val-Cys-Gly-Glu-Arg-Xaa6-Xaa7-

Xaa8-Tyr-Thr-Pro-Lys-Thr wherein
Xaa5 is glycine or alanine,
Xaa6 is glycine or alanine,
Xaa7 is phenylalanine or alanine, and
Xaa8 is phenylalanine or alanine,
with the proviso that the peptide comprising the A-chain of SEQ ID NO: 39 and the B-chain of SEQ ID NO: 40 is excluded.

2. The long-acting insulin of claim 1, wherein the biocompatible material is selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer.

3. The long-acting insulin of claim 1, wherein the insulin analog and the biocompatible material are linked to each other by a peptide bond.

4. The long-acting insulin of claim 1, wherein the insulin analog and the biocompatible material are linked by a linker selected from the group consisting of polyethylene glycol, fatty acid, saccharide, a polymer, a low molecular weight compound, a nucleotide, and a combination thereof.

5. The long-acting insulin of claim 1, wherein the insulin analog and the biocompatible material are linked by a linker interposed therebetween, and the biocompatible material is an FcRn-binding material, wherein the linker is a peptide linker, or a non-peptide linker selected from the group consisting of polyethylene glycol, polypropylene glycol, an ethylene glycol-propylene glycol copolymer, polyoxytheylated polyol, polyvinyl alcohol, polysaccharide, dextran, polyvinyl ether, a biodegradable polymer, a lipid-polymer, chitins, hyaluronic acid, and a combination thereof.

6. The long-acting insulin of claim 5, wherein the FcRn-binding material is a polypeptide comprising an immunoglobulin Fc region.

7. The long-acting insulin of claim 5, wherein each end of the non-peptide linker is respectively linked to an amine group or thiol group of the biocompatible material and the insulin analog.

8. A method for preparing the long-acting insulin of claim 1, comprising:
(a) providing (i) an insulin analog; and (ii) a biocompatible material selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue or a derivative thereof, a nucleotide, fibronectin, transferrin, saccharide, and a polymer, respectively; and (b) linking the insulin analog to the biocompatible material,
wherein the insulin analog includes the A chain of SEQ ID NO: 37 of Formula 1 below and the B chain of SEQ ID NO: 38 of Formula 2 below:

Formula 1:

Xaa1-Xaa2-Val-Glu-Gln-Cys-Cys-Thr-Ser-Ile-Cys-
Ser-Leu-Xaa3-Gln-Leu-Glu-Asn-Xaa4-Cys-Asn (SEQ ID NO: 37)

wherein:
Xaa1 is glycine,
Xaa2 is isoleucine or alanine,
Xaa3 is tyrosine, glutamic acid, or asparagine, and
Xaa4 is tyrosine or alanine; and Formula 2:

Phe-Val-Asn-Gln-His-Leu-Cys-Xaa5-Ser-His-Leu-
Val-Glu-Ala-Leu-Tyr-Leu-Val-Cys-Gly-Glu-Arg-
Xaa6-Xaa7-Xaa8-Tyr-Thr-Pro-Lys-Thr (SEQ ID NO: 38)

wherein:
Xaa5 is glycine or alanine,
Xaa6 is glycine or alanine,
Xaa7 is phenylalanine or alanine, and
Xaa8 is phenylalanine or alanine,
with the proviso that the peptide comprising the A-chain of SEQ ID NO: 39 and the B-chain of SEQ ID NO: 40 is excluded.

9. A long-acting insulin formulation with improved in-vivo duration and stability comprising the long-acting insulin of claim 1.

10. A long-acting insulin formulation for the treatment of diabetes comprising the long-acting insulin of claim 1.

11. The long-acting insulin of claim 1, wherein the insulin analog comprises:
(i) the A-chain, wherein, in Formula 1, Xaa1 is glycine, Xaa2 is alanine, Xaa3 is tyrosine, and Xaa4 is tyrosine; and the B-chain, wherein, in Formula 2, Xaa5 is glycine, Xaa6 is glycine, Xaa7 is phenylalanine, and Xaa8 is phenylalanine;
(ii) the A-chain, wherein, in Formula 1, Xaa1 is glycine, Xaa2 is isoleucine, Xaa3 is glutamic acid or asparagine, and Xaa4 is tyrosine; and the B-chain, wherein, in Formula 2, Xaa5 is glycine, Xaa6 is glycine, Xaa7 is phenylalanine, and Xaa8 is phenylalanine;
(iii) the A-chain, wherein, in Formula 1, Xaa1 is glycine, Xaa2 is isoleucine, Xaa3 is tyrosine, and Xaa4 is alanine; and the B-chain, wherein, in Formula 2, Xaa5 is glycine, Xaa6 is glycine, Xaa7 is phenylalanine, and Xaa8 is phenylalanine;
(iv) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is alanine, Xaa6 is glycine, Xaa7 is phenylalanine, and Xaa8 is phenylalanine;
(v) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is glycine, Xaa6 is alanine, Xaa7 is phenylalanine, and Xaa8 is phenylalanine;
(vi) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is glycine, Xaa6 is glycine, Xaa7 is alanine, and Xaa8 is phenylalanine; or
(vii) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is glycine, Xaa6 is glycine, Xaa7 is phenylalanine, and Xaa8 is alanine.

12. A conjugate of the following Chemical Formula 1:

X—La—F                       Chemical Formula 1:

wherein X is an insulin analog having reduced insulin receptor binding affinity compared to the native insulin,
L is a linker,
a is 0 or a natural number, with the proviso that each L is independent from each other when a is 2 or higher, and
F is a material capable of increasing the in-vivo half-life of the insulin analog,
wherein the insulin analog includes the A chain of SEQ ID NO: 37 of Formula 1 below and the B chain of SEQ ID NO: 38 of Formula 2 below:

Formula 1:

Xaa1-Xaa2-Val-Glu-Gln-Cys-Cys-Thr-Ser-Ile-Cys-
Ser-Leu-Xaa3-Gln-Leu-Glu-Asn-Xaa4-Cys-Asn (SEQ ID NO: 37)

wherein:
Xaa1 is glycine,
Xaa2 is isoleucine or alanine,
Xaa3 is tyrosine, glutamic acid, or asparagine, and
Xaa4 is tyrosine or alanine; and Formula 2:

Phe-Val-Asn-Gln-His-Leu-Cys-Xaa5-Ser-His-Leu-
Val-Glu-Ala-Leu-Tyr-Leu-Val-Cys-Gly-Glu-Arg-
Xaa6-Xaa7-Xaa8-Tyr-Thr-Pro-Lys-Thr (SEQ ID NO: 38)

wherein:
Xaa5 is glycine or alanine,
Xaa6 is glycine or alanine,
Xaa7 is phenylalanine or alanine, and
Xaa8 is phenylalanine or alanine,
with the proviso that the peptide comprising the A-chain of SEQ ID NO: 39 and the B-chain of SEQ ID NO: 40 is excluded.

13. The conjugate of claim 12, wherein the material capable of increasing the in-vivo half-life of the insulin analog is selected from the group consisting of polyethylene glycol, fatty acid, cholesterol, albumin and a fragment thereof, an albumin-binding material, a polymer of repeating units of a particular amino acid sequence, an antibody, an antibody fragment, an FcRn-binding material, in-vivo connective tissue, a nucleotide, fibronectin, transferrin, saccharide, and a polymer.

14. The conjugate of claim 12, wherein L is selected from the group consisting of a peptide, polyethylene glycol, fatty acid, saccharide, a polymer, a low molecular weight compound, a nucleotide, and a combination thereof.

15. The conjugate of claim 14, wherein the polymer is a non-peptide linker selected from the group consisting of polypropylene glycol, ethylene glycol-propylene glycol copolymer, polyoxytheylated polyols, polyvinyl alcohols, polysaccharides, dextran, polyvinyl ether, biodegradable polymers, lipid-polymers, chitins, hyaluronic acid, oligonucleotides, and a combination thereof.

16. The conjugate of claim 12, wherein X and F are linked by L through a covalent chemical bond, a non-covalent chemical bond, or a combination thereof.

17. The conjugate of claim 12, wherein F is an IgG Fc region.

18. The conjugate of claim 12, wherein the insulin analog comprises:
(i) the A-chain, wherein, in Formula 1, Xaa1 is glycine, Xaa2 is alanine, Xaa3 is tyrosine, and Xaa4 is tyrosine;

and the B-chain, wherein, in Formula 2, Xaa5 is glycine, Xaa6 is glycine, Xaa7 is phenylalanine, and Xaa8 is phenylalanine;

(ii) the A-chain, wherein, in Formula 1, Xaa1 is glycine, Xaa2 is isoleucine, Xaa3 is glutamic acid or asparagine, and Xaa4 is tyrosine; and the B-chain, wherein, in Formula 2, Xaa5 is glycine, Xaa6 is glycine, Xaa7 is phenylalanine, and Xaa8 is phenylalanine;

(iii) the A-chain, wherein, in Formula 1, Xaa1 is glycine, Xaa2 is isoleucine, Xaa3 is tyrosine, and Xaa4 is alanine; and the B-chain, wherein, in Formula 2, Xaa5 is glycine, Xaa6 is glycine, Xaa7 is phenylalanine, and Xaa8 is phenylalanine;

(iv) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is alanine, Xaa6 is glycine, Xaa7 is phenylalanine, and Xaa8 is phenylalanine;

(v) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is glycine, Xaa6 is alanine, Xaa7 is phenylalanine, and Xaa8 is phenylalanine;

(vi) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is glycine, Xaa6 is glycine, Xaa7 is alanine, and Xaa8 is phenylalanine; or (vii) the A-chain, wherein, in Formula 1, Xaa1 is glycine, Xaa2 is isoleucine, Xaa3 is tyrosine, and Xaa4 is tyrosine; and the B-chain, wherein, in Formula 2, Xaa5 is glycine, Xaa6 is glycine, Xaa7 is phenylalanine, and Xaa8 is alanine.

* * * * *